United States Patent
Herrmann et al.

(10) Patent No.: US 9,987,217 B2
(45) Date of Patent: Jun. 5, 2018

(54) BLACKBERRY EXTRACT

(75) Inventors: Martina Herrmann, Hameln (DE);
Holger Joppe, Dassel (DE); Helge Franke, Dieburg (DE); Gabriele Vielhaber, Holzminden (DE)

(73) Assignee: Symrise AG, Holzminden (DE)

(*) Notice: Subject to any disclaimer, the term of this patent is extended or adjusted under 35 U.S.C. 154(b) by 1018 days.

(21) Appl. No.: 11/629,753

(22) PCT Filed: Jun. 16, 2005

(86) PCT No.: PCT/EP2005/052793
§ 371 (c)(1),
(2), (4) Date: May 30, 2007

(87) PCT Pub. No.: WO2005/123101
PCT Pub. Date: Dec. 29, 2005

(65) Prior Publication Data
US 2008/0095719 A1    Apr. 24, 2008

Related U.S. Application Data

(60) Provisional application No. 60/581,307, filed on Jun. 18, 2004, provisional application No. 60/654,380, filed on Feb. 18, 2005.

(51) Int. Cl.
| *A61K 8/97* | (2017.01) |
| *A61K 36/73* | (2006.01) |
| *A61Q 11/00* | (2006.01) |
| *A61Q 19/08* | (2006.01) |

(52) U.S. Cl.
CPC ............... *A61K 8/97* (2013.01); *A61K 36/73* (2013.01); *A61Q 11/00* (2013.01); *A61Q 19/08* (2013.01); *A61K 2800/782* (2013.01)

(58) Field of Classification Search
CPC ...... A61K 8/97; A61K 36/73; A61K 2300/00; A61K 2800/782; A61Q 11/00; A61Q 19/00
See application file for complete search history.

(56) References Cited

U.S. PATENT DOCUMENTS

| 2003/0104076 A1* | 6/2003 | Berkulin | A61K 36/28 424/725 |
| 2003/0203054 A1 | 10/2003 | Selzer et al. | |
| 2004/0009244 A1* | 1/2004 | Kim | A23L 1/3002 424/729 |

FOREIGN PATENT DOCUMENTS

| JP | 02084486 A | * 3/1990 |
| JP | 05255101 A | * 10/1993 |
| JP | 05269187 A | * 10/1993 |
| JP | 09118627 A | * 5/1997 |
| JP | 11124322 A | * 5/1999 |
| JP | 2002226357 A | * 8/2002 |
| JP | 2003160433 A | * 6/2003 |
| JP | 2003183122 A | * 7/2003 |
| JP | 2003-335647 | 11/2003 |
| WO | 03/039515 | 5/2003 |

OTHER PUBLICATIONS

Green, J. The Herbal Medicine-Maker's Handbook: A Home Manual, 2000. The Crossing Press, U.S.A. Chapter 5: The Extraction Process; and, Chapter 6: Solvents, pp. 74-98.*
Derwent Abstract of JP 2003-160433.
Schade et al., Use of a Plant-Derived Enzyme Template for the Production of the Green-Note Volatile Hexanal, Biotechnology and Bioengineering, vol. 84, No. 3, Nov. 5, 2003.
Derwent Abstract XP-002343401 of JP 2003-160433, Jun. 3, 2003.
Derwent Abstract XP-002346786 of JP 10-08054, Jan. 14, 1986.
Yasuda et al., Deodorant Effect of Plant Extracts of the Family Rosaceae against Methyl Mercaptan, 1992, Nippon Nogeikagaku Kaishi, vol. 66, Nr. 10, pp. 1475-1479, XP-009053179.
Garcia-Alonso et al., Assessment of the Antioxidant Properties During Storage of a Dessert Made from Grape, Cherry, and Berries, Journal of Food Science, vol. 68, Nr. 4, 2003, pp. 1525-1530.
Niederauer, Gelier- und Verdickungsmittel Herstellung, Eigenschaften under Anwendung von Gelier under Verdickungsmitteln, 1995, XP009081769.
Nippon Nag. Kaishi, Deodorant Effect of Plant Extracts of the Family Rosaceae Against Methyl Mercaptan, vol. 66, No. 10, 1992, pp. 1475-1479.
Japanese Office Action dated Sep. 12, 2011 in JP 2007-515959.

* cited by examiner

*Primary Examiner* — Amy Lynn Clark
(74) *Attorney, Agent, or Firm* — Dilworth & Barrese, LLP

(57) ABSTRACT

The invention concerns a blackberry leaf extract and its uses, in particular to slow down skin aging, to treat the oral and pharyngeal cavity, and there in particular to prevent and slow down periodontitis and the excessive degradation of the periodontal connective tissue as well as damage to the teeth caused by matrix metalloproteinases.

7 Claims, 1 Drawing Sheet

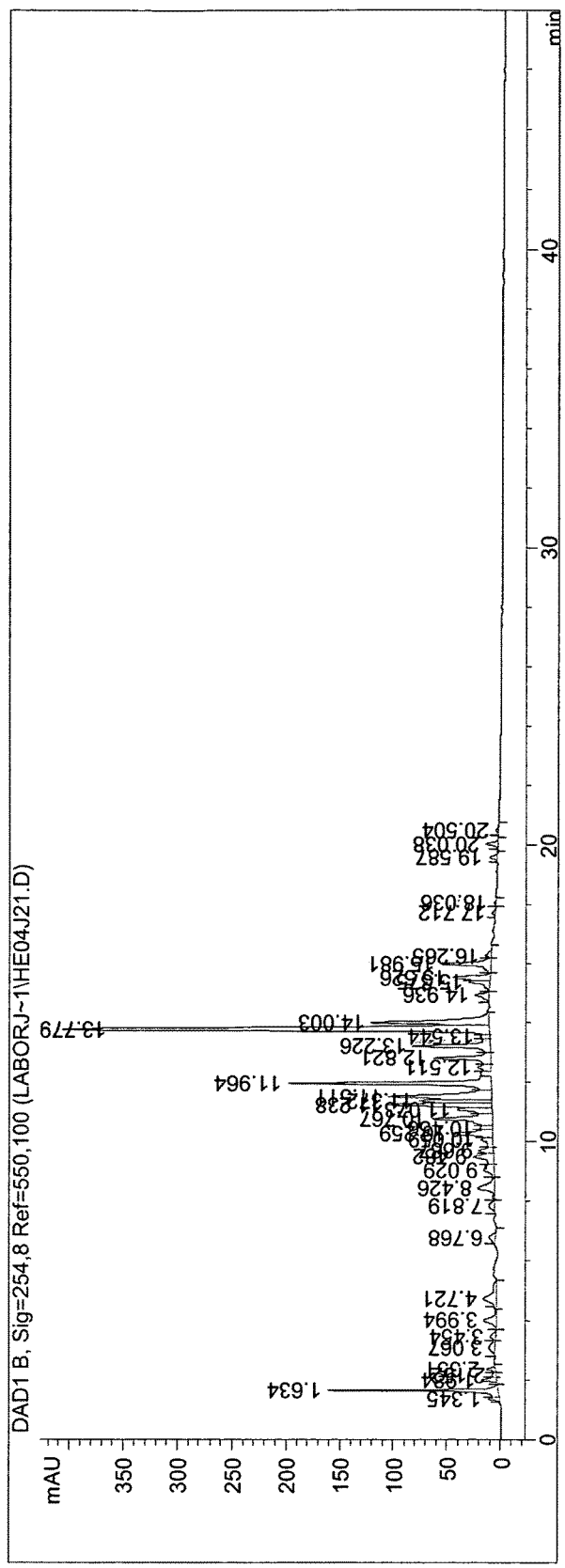

BLACKBERRY EXTRACT

This application claims priority to U.S. Provisional Application No. 60/581,307 filed on Jun. 18, 2004 and U.S. Provisional Application No. 60/654,380 filed on Feb. 18, 2005

FIELD OF THE INVENTION

The invention concerns the field of plant extracts and their uses, in particular for oral hygiene, cosmetic and pharmaceutical purposes. The invention especially concerns the production of blackberry leaf extracts, the extracts themselves and their use to inhibit matrix metalloproteinases (MMPs), in particular to slow down skin ageing, to treat the oral and pharyngeal cavity, and there in particular to prevent and slow down periodontitis and the excessive degradation of periodontal connective tissue and damage to the teeth caused by matrix metalloproteinases.

BACKGROUND OF THE INVENTION

The aging of human skin is accompanied by increasing formation of wrinkles and reducing elasticity and strength. A distinction is made in the ageing process between intrinsic and extrinsic skin ageing. Intrinsic ageing includes natural changes to the skin, which are regulated by genetic makeup. The term extrinsic skin ageing stands for premature ageing processes brought about by exogenous influences such as sunlight, environmental pollutants (for example ozone, tobacco smoke, etc.), psychological stress and chronic inflammation. Ultraviolet radiation is the most important exogenous pathogen leading to premature ageing of the human skin (light ageing). In addition to natural sunlight, irradiation of the human skin with artificial UV radiation (solarium) is playing an ever greater role.

The structural changes responsible for the clinical image of aged skin take place primarily in the dermis. Elasticity and strength of the skin are determined substantially by the two main constituents of the dermal extracellular matrix, the two fibre proteins collagen and elastin. The dermis contains mainly collagen-1 (90-85%), which is formed exclusively from dermal fibroblasts, and, in significantly smaller amounts (10-15%), collagen-3. Elastin, the principal component of the elastic fibres of the skin apart from fibrillin, is contained in the dermis in a proportion of around 1-3%.

In comparison to young skin, old skin is characterised by a lowering concentration of collagen and elastin. This age-related loss of tissue is at least partially caused by an imbalance between activation and inhibition of proteolytic activity. An important role is played here by matrix metalloproteinases, a group of enzymes which are able to break down the macromolecules in the extracellular matrix (ECM) proteolytically. Thus it has been found that the content of MMPs is markedly higher in old skin than in young skin (J. H. Chung et al., J. Invest. Dermatol, 2001, 117, 1218-1224).

MMPs have a broad, often overlapping, substrate specificity, and when combined they are capable of destroying all protein components of the extracellular matrix. Some 20 MMPs have been identified to date. They are generally secreted as inactive pro-enzymes (pro-MMP). Of particular importance in the human skin are, above all, MMP-1 (collagenase-1), MMP-2 (gelatinase A), MMP-9 (gelatinase B) and MMP-3. In addition to collagen-1 and -3, MMP-1 also cleaves pro-MMP-2 and pro-MMP-9, thereby causing them to be activated. MMP-2 and MMP-9 belong to the elastin-degrading proteases (A. Thibodeau, Cosmetics & Toiletries 2000, 115 (11), 75-82).

MMPs also play a critical role in the premature skin aging caused by exogenous factors. Thus, an even higher level of MMPs was detected in light-aged skin as compared with aged skin protected from the light (J. H. Chung et al., J. Invest. Dermatol, 2001, 117, 1218-1224). The induction of matrix metalloproteinases was detected both for UVA and UVB and for infrared radiation. This induction was able to be observed both in vitro on cultivated human dermal fibroblasts and in vivo on UV-irradiated human skin. Stimulation with tobacco smoke also led in human dermal fibroblasts to an induction of the expression of MMP-1 and -3 (J. Krutmann, Hautarzt 2003, 54, 809-817).

The regulation of MMP activity can occur at three levels: at a transcription level, in the conversion of pro-MMP to the active form or by inactivation of MMPs by inhibitors.

The reproduction of the imbalance in the proteolytic activity of MMPs, in particular MMP-1, -2, -3 and -9, brought about by intrinsic and extrinsic skin ageing is thus an important objective in the development of new cosmetic active ingredients against skin ageing and wrinkles.

The use of MMP-1-inhibiting substances (retinyl palmitate, propyl gallate, precocene, 6-hydroxy-7-methoxy-2,2-dimethyl-1(2H)-benzopyran, 3,4-dihydro-6-hydroxy-7-methoxy-2,2-dimethyl-1(2H)-benzopyran) to prevent sunlight- and/or heat-induced ageing of the human skin was described in the laid-open specification WO 01/74320.

Matrix metalloproteinases are also significant in pathological changes to the periodontium. Periodontitis is an inflammation of the periodontium, in other words the tissues that surround and support the teeth. The periodontium comprises various tissues: the gum epithelium (gingiva), the connective tissue of the gingiva, the periodontal ligament (desmodontium), the cementum and the surrounding alveolar bone. The desmodontium is located between the surface of the root and the alveolar bone. It is a cell-rich connective tissue which holds the tooth in the bony tooth socket, the alveolus. 53 to 74% of the periodontal space is made up of collagen and oxytalan fibre bundles. The portion of the periodontal fibres incorporated into the cementum and the alveolar bone holds the tooth in the alveolus. The main clinical features of periodontitis include inflammation of the gums, attachment loss, formation of periodontal pockets and degradation of the alveolar bone.

The main cause of periodontitis is plaque. This consists of certain components of saliva, food residues and above all bacteria and their decomposition products. This special form of an infectious disease is caused in most cases by *Porphyromonas gingivalis, Bacteroides forsythus* and *Actinobacillus actinomycetemcomitans*. The continuous release of bacterial toxins, especially of lipopolysaccharides, presumably triggers the distribution of proinflammatory mediators, such as IL-1beta, TNF-alpha and PGE2 for example, in the patient's affected tissues. These signal substances stimulate the infiltration of immunocompetent cells into the populated tissue. The migration of neutrophilic granulocytes and macrophages then subsequently leads to inflammation of the gums (gingivitis) and to the release of proinflammatory mediators such as IL-1 and IL-6, for example. These in turn activate in the skin and mucous membranes the synthesis of matrix-degrading metalloproteinases (matrix metalloproteinases, MMPs), which destroy the extracellular matrix of the surrounding connective tissue. This allows bacteria, which initially interacted with the free gingiva, to penetrate further into the underlying connective tissue, continuing inflammation processes and the synthesis of MMPs there and finally loosening the connection between the uppermost layer of the epithelium and the root of the tooth. A gingival pocket is formed as a consequence. The reaction of the body is the inflammation of the gingiva and the periodontium with damage to the alveolar bone. In the final stage of periodontitis the affected person is at risk of a massive loss of teeth.

Studies (T. Kuboto et al., Arch. Oral. Biol. 1996, 41, 253-262; A. L. Ejeil et al., J. Periodontol. 2003, 74, 188-195) have shown that the levels of a series of matrix metalloproteinases (MMP-1, -3, -8, -9 and -13) are significantly higher in patients with inflammation of the gums than in patients with healthy gums. The level correlates with the severity of the gingivitis or periodontitis. Furthermore, collagen fibres decrease significantly as the inflammation of the gums becomes more marked. MMP-9 clearly acts as a marker here at an early stage of periodontitis (A. L. Ejeil et al., J. Periodontol. 2003, 74, 188-195).

MMPs also have an important role to play in the development of caries and non-caries-related losses of hard tooth structure, such as erosions for example. The teeth are constructed mainly from a bonelike substance called dentine. In the area of the crown which protrudes from the gum, the dentine is covered with the protective enamel. Dentine is made up of around 30% of a cell-free basic substance consisting largely of glycoproteins. Collagen fibres and inorganic components are incorporated herein.

The development of caries and erosions is accompanied by the demineralisation of the teeth. Mineral substances are critically responsible for the hardness of the tooth. The formation of acids by oral bacteria after consumption of sugary foods on the one hand, but also through frequent contact with highly acidic drinks (e.g. fruit juices) and highly acidic food (citrus and tropical fruits, pineapple, etc.) leads to demineralisation of the enamel and, if it continues, of the dentine too. The demineralised dentine is susceptible to degradation. It has been shown in vitro that the degradation of the organic matrix is necessary for the development of a cavity in the tooth. Tjäderhane et al. (J. Dent. Res. 1998, 77, 1622-1629) detected MMP-2, MMP-8 and MMP-9 in caries lesions and established that these are activated by acids.

Pashley et al. (J. Dent. Res. 2004, 83, 216-221) showed that even in the absence of bacteria, degradation of collagen fibres in the organic matrix occurs in dentine which has been partially demineralised by acid, due to collagenolytically active proteases. The degradation of the collagen fibres was prevented by the addition of chlorhexidine or protease inhibitors (MMP inhibitor: benzamidine hydrochloride, cysteine proteinase inhibitor: N-ethyl maleimide, epsilon-amino-n-hexanoic acid, serine protease inhibitor: phenylmethylsulfonyl fluoride).

Maintaining the health or slowing the degradation of the connective tissue of the periodontium and the collagen fibres of the teeth by preventing damage due to MMPs is therefore an important aim in the development of new active ingredients for the area of oral care and oral hygiene. In order to stop the processes described effectively, the damage caused by MMPs and in particular here by MMP-1 (collagenase-1), MMP-2 (gelatinase A), MMP-8 (collagenase-2) and MMP-9 (gelatinase B) must be inhibited at a very early stage.

The use of synthetic MMP inhibitors in periodontal diseases has been described in several publications (M. E. Ryan et al., Curr. Opin. Periodontal. 1996, 3, 85-96; R. Gendron et al., Clin. Diagn. Lab. Immunol. 1999, 6, 437-439).

A number of plant extracts have also already been described as inhibitors of various MMPs. For instance, numerous plant extracts, and the inhibition of various proteases, including several MMPs, that can be achieved with them, are described in laid-open specification WO 02/069992 A1, although no conclusions can be drawn as to the concentrations of extract used and the precise extraction conditions. From the results tables reproduced in the cited laid-open specification, no correlation can be identified between a specific plant family or a specific plant species and the effectiveness of a corresponding plant extract in the inhibition of metalloproteinases.

In Ann. Pharmaceutiques Françaises 1990, 48, 335-340 and in the European patent application EP 0283349 A, J. L. Lamaison describes the inhibition of elastase (porcine pancreatic elastase) and collagenase with extracts of plants selected from the rosaceae group and attributes the inhibition to the tannins they contain.

Ethanol and acetone extracts from *Rubus fruticosus* and other plants, which are to be used to prevent skin ageing, are known from Japanese laid-open specification JP 2003-160433. Production of the extracts is a lengthy process, however (extraction period: 1 week).

In the Commission E monograph, blackberry leaves in the form of aqueous tea infusions and mouthwashes are indicated inter alia for the area of application of mild inflammations of the mucous membranes of the mouth and pharynx (Bundesanzeiger, 1 Feb. 1990, issue number 22a, no. 01071). The effectiveness is attributed to the astringent effect of the tannins they contain. No mention is made, however, of the treatment of damage to the connective tissue of the periodontium and to the collagen fibres of the teeth caused by MMPs.

SUMMARY OF THE INVENTION

An object of the present invention was to specify agents for preventing or slowing down damage to an extracellular matrix. Agents should be specified in particular for slowing down the ageing of the skin and for protecting the skin and mucous membranes of the periodontium and for protecting the organic matrix of the dentine from damage and/or from excessive degradation. If an application for the skin of a user is sought, the agents according to the invention should if possible be particularly effective against extrinsic skin ageing and the associated exogenous influencing factors. The agents to be specified should if possible be natural in origin, easy to produce, readily storable and usable in many different preparations, particularly in cosmetic and pharmaceutical preparations and in preparations for oral hygiene. Production methods for corresponding agents and their uses should also be specified.

An oral hygiene product (also referred to below as an oral care product or oral hygiene preparation) within the meaning of the invention is understood to be one of the formulations familiar to the person skilled in the art for cleansing and care of the oral cavity and pharynx and for freshening the breath. This expressly includes care of the teeth and gums. Pharmaceutical forms of common oral hygiene formulations are creams, gels, pastes, foams, emulsions, suspensions, aerosols, sprays and also capsules, granules, pastilles, tablets, sweets or chewing gums, wherein this list should not be understood as being limiting for the purposes of this invention.

DETAILED DESCRIPTION OF THE INVENTION

Surprisingly it has been found in extensive in-house investigations that an extract of the leaves of the blackberry (*Rubus fruticosus*) exhibits an outstanding MMP-9- and MMP-1-inhibiting action. It was also established that in comparison to the leaf extract, a blackberry fruit extract or juice concentrate which was also tested displays a markedly lower anti-MMP-1 and -9 activity.

According to the invention a process is therefore specified for the production of a blackberry leaf extract, comprising the following steps:
a) Addition to blackberry leaves of an extractant containing an alcohol selected from the group consisting of methanol, ethanol, n-propanol, iso-propanol,
b) Extraction of the blackberry leaves with the extractant for up to 72 hours.

Extracts produced in this way have proved to be particularly effective in inhibiting the metalloproteinases MMP-1 and MMP-9, even in low concentrations.

FIG. 1 is an HPLC diagram obtained from Example 1.

Surprisingly, extracts of other rosaceae leaves do not allow the inhibition of the metalloproteinases MMP-1 and MMP-9 that is achievable with the extracts according to the invention described above even in low concentrations. For example, raspberry leaf extract in comparison to blackberry leaf extract in the same concentration displays a 28 times lower anti-MMP-9 activity and a 6 times lower anti-MMP-1 activity (see the appended examples), even though the raspberry (*Rubus idaeus*) is a member of the same plant species as the blackberry.

In contrast to the fruit, little characterisation has so far been undertaken with regard to the constituents of the leaves of the blackberry. According to J. L. Lamaison (see above), the anti-elastase and anti-collagenase activity should correlate with the tannin content. Astonishingly, our own investigations could not confirm this, however. Although our determination of the total polyphenol content of various blackberry leaf extracts likewise resulted in relatively high polyphenol contents, no correlation could be found between polyphenol content and activity (see examples). Thus, for example, an extract produced with water as the extractant, in comparison to an extract produced with an ethanol/water 3:7 extractant, displayed a comparable tannin content but a 50 times lower activity in the anti-MMP-9 assay and a 10 times lower activity in the anti-MMP-1 assay. Dried blackberry leaves are preferably used. It is also preferable to use only blackberry leaves for the extraction and not also other plant parts such as the berries of the blackberry or its branches and roots.

A further advantage of the blackberry leaf extract according to the invention and thus also of its production process according to the invention is that it can be largely or completely decolourised with conventional chlorophyll removal methods, for example by the addition of activated carbon or bleaching clay directly during extraction or in a subsequent step, without its losing its matrix metalloproteinase-inhibiting action. The extract additionally exhibits only a slight inherent odour. Both are particularly advantageous in cosmetics and above all in the area of leave-on products, since the extract according to the invention thus leads to little or no change in the appearance and odour of a cosmetic preparation containing the extract even in high concentrations. Furthermore, the extract has a slight, pleasant, herbal, green, tea-like inherent flavour reminiscent of camomile and peppermint. This makes it additionally suitable for use in oral hygiene products, since for use in the oral cavity the flavour is an important acceptance criterion for users and thus ultimately also determines the success of an application of the oral hygiene product.

Particularly preferred extracts can be produced with extractants which contain ethanol as the alcohol component. These extractants, unlike methanol-containing types, for example, are comparatively safe to use and easy to obtain in a technically adequate grade. In particularly preferred processes and for the production of correspondingly preferred extracts, the extractant contains only one alcohol, preferably ethanol. The person skilled in the art is aware that, particularly when technical alcohol is used, other constituents can also be contained in the extractant as impurities; such impurities are not important for the success of the extraction process according to the invention.

The ratio of the mass of extractant to leaf solids is preferably established such that at least a 10-fold mass of extractant relative to the leaf solids and preferably no more than a 50-fold mass of extractant relative to the leaf solids is obtained, preferably a 10- to 20-fold mass. A 14- to 18-fold mass of extractant relative to the leaf solids is particularly preferably used for extraction. Good results were achieved with a 16-fold mass of an ethanol-containing solvent (relative once again to the leaf solids).

The extraction time for performing step b) is at most 72 hours but can also be shorter. With particularly short extraction times only a very dilute extract is obtained in step b). It is therefore preferable to extract the blackberry leaves in step b) for at least 1 hour, in particular for at least 2 hours. The extraction time needed to obtain an extract for use in producing cosmetic, oral hygiene and/or pharmaceutical preparations or drugs is preferably at most 24 hours and particularly preferably at most 4 hours. The necessary extraction time is chosen on the basis of the quality of the blackberry leaves to be extracted, particularly their age, and of the other extraction conditions, particularly the extraction temperature. At elevated extraction temperatures, in particular at an extraction temperature in the range from 60 to 100° C., preferably in the range from 80 to 100° C., the extraction time is preferably 1 h to 6 h and particularly preferably 2 h to 4 h.

In addition, it is particularly preferable to perform the extraction in step b) by refluxing the extractant, particularly at extraction temperatures in the range from 60 to 100° C., preferably in the range from 80 to 100° C. In this case the extraction time is preferably no more than 24 hours, extracts having a readily usable composition for use in producing cosmetic, oral hygiene and/or pharmaceutical preparations or drugs being obtained with an extraction lasting just 2 to 4 hours.

The extraction temperature is established on the basis of the extractant that is used. If an ethanol-containing solvent is used, an extraction temperature in the range from 60° C. to 100° C., in particular an extraction temperature in the range from 80° C. to 100° C., is preferred, particularly if a mixture of ethanol and water is used as the extractant, see below.

It is preferable if the extractant contains the alcohol, particularly ethanol, in a proportion of at least 20 wt. %, relative to the total extractant. It is likewise preferable if the extractant contains water in a proportion of at least 15 wt. %, relative to the total extractant. It is particularly preferable if the extractant simultaneously contains both at least 20 wt. %, relative to the total extractant, of an alcohol (preferably ethanol) and water in a proportion of at least 15 wt. %, relative to the total extractant. Surprisingly it was established that pure water or ethanol extracts demonstrated a lower anti-MMP action than extracts produced using ethanol/water blends. Particularly preferred blackberry leaf extracts are obtained with an extractant consisting of ethanol and water in the ratio of 2:8 (2 parts by weight of ethanol mixed with 8 parts by weight of water) to 8:2, preferably in the ratio of 3:7 to 7:3 and particularly preferably in the ratio of 3:7 to 1:1. This particularly applies if the blackberry leaf extract according to the invention or a preparation containing the extract is to be used to inhibit MMP-9.

The blackberry leaf extract according to the invention can preferably be processed further to form a blackberry leaf extract according to the invention in solid form, by extending the production process according to the invention by means of the following steps:

c) Optional addition to the extract of a solid support which is acceptable for pharmaceutical, oral hygiene and/or cosmetic purposes, and d) Drying of the extract with the support optionally added in step c) to a residual content of extractant of at most 5 wt. %, relative to the total weight of the extract obtained in step d).

Step c) can also be omitted according to the invention, in which case a more highly concentrated powder is obtained than if a support is added which is acceptable for oral hygiene, pharmaceutical and/or cosmetic purposes. A solid which is at least non-toxic for the organism on which it is to be used is acceptable for pharmaceutical, oral hygiene or cosmetic purposes. Preferred solids which are acceptable for cosmetic, oral hygiene or pharmaceutical purposes are powdered maltodextrin, lactose, silicon dioxide or glucose and mixtures of two or more of these solids. A particularly preferred acceptable solid according to the invention for oral hygiene purposes is silicon dioxide. Other acceptable solids according to the invention for oral hygiene purposes are hydrocolloids such as starches, degraded starches, chemically or physically modified starches, modified celluloses, gum arabic, gum ghatti, tragacanth gum, karaya, carrageenan, pullulan, curdlan, xanthan gum, gellan gum, guar gum, locust bean gum, alginates, agar, pectin and inulin as well as mixtures of two or more of these solids, particularly also with silicon dioxide.

Particularly preferred according to the invention is a production process and correspondingly a blackberry leaf extract wherein the extract obtained in step b), optionally together with a support which is acceptable for oral hygiene purposes, pharmaceutically and/or cosmetically, such as preferably maltodextrin and/or glucose, is processed further by spray drying to form a powder. Extracts according to the invention having a long shelf life can be obtained in this way which are particularly suitable in particular for further processing for the uses according to the invention as described here. In addition, the final concentration of the active ingredients contained in the extract powder can be advantageously easily adjusted by adjusting the mixing ratio of the extract obtained in step b) and the support that is acceptable for oral care, pharmaceutical and/or cosmetic purposes. A preferred blackberry leaf extract according to the invention in powder form is produced by mixing maltodextrin and the liquid native blackberry leaf extract obtained in step b) in a mixing ratio of 10 parts by weight of native extract to 90 parts by weight of maltodextrin. "Native extract" refers here to the extract that is obtained when the extractant is eliminated from the extract obtained in step b).

The solid or liquid blackberry leaf extract can moreover also be processed further according to the invention to form a liquid preparation, by mixing the blackberry leaf extract with a solvent chosen from the group consisting of glycerol, 1,2-propylene glycol, 1,3-butylene glycol, ethanol, water and mixtures of two or more of the cited solvents with water.

Such extracts produced according to the invention are particularly readily able to be processed further for cosmetic and oral hygiene purposes. These preparations according to the invention can optionally be produced with the addition of a preservative, solubiliser or antioxidant.

The solid or liquid blackberry leaf extract or the liquid or solid preparation containing blackberry leaf extract can also be processed further according to the invention by encapsulation. According to the invention the blackberry leaf extract and/or the liquid or solid preparation containing it is encapsulated with a solid shell material, which is preferably selected from starches, degraded or chemically or physically modified starches (in particular dextrins and maltodextrins), gelatines, gum arabic, agar-agar, gum ghatti, gellan gum, modified and unmodified celluloses, pullulan, curdlan, carrageenans, alginic acid, alginates, pectin, inulin, xanthan gum and mixtures of two or more of the cited substances.

The solid shell material is preferably selected from gelatine (pork, beef, poultry and/or fish gelatines and mixtures thereof are advantageous, preferably including at least one gelatine having a Bloom value of greater than or equal to 200, preferably having a Bloom value of greater than or equal to 240), maltodextrin (preferably obtained from maize, wheat, tapioca or potato, preferred maltodextrins displaying a DE value in the range from 10 to 20), modified cellulose (e.g. cellulose ether), alginates (e.g. Na alginate), carrageenan (beta-, iota-, lambda- and/or kappa-carrageenan), gum arabic, curdlan and/or agar-agar. Gelatine is used in particular because of its good availability in various Bloom values. Particularly preferred for oral hygiene purposes in particular are seamless gelatine or alginate capsules, whose shell dissolves very quickly in the mouth or bursts when chewed, thus releasing the active ingredient in the oral cavity. Production can take place as described for example in EP 0 389 700, JP 7 196 478, U.S. Pat. No. 4,251,195, U.S. Pat. No. 6,214,376, WO 03/055587 or WO 2004/050069.

Blackberry leaf extract can advantageously used anywhere in cosmetics where cosmetically desirable effects are linked to MMP inhibition. It is preferably used, however, as an active ingredient against natural and against premature, for example sunlight-induced, skin ageing and wrinkles. To this end it is preferably applied topically to the skin to be treated.

Substantial areas of application here are cosmetic, particularly dermatological, preparations which (except for the presence of blackberry leaf extract) have a conventional composition and are used for cosmetic, particularly dermatological, protection against light, for the treatment, care and cleansing of the skin and/or hair or as a makeup product in decorative cosmetics. Such preparations, depending on their structure, can accordingly be used as, for example, a skin care cream, day or night cream, eye cream, sunscreen or after-sun lotion, skin food, conditioning mask, gel pads, face lotion, moist conditioning and cleansing cloths, cleansing milk, cleansing soap, foam bath or shower gel, deodorant, antiperspirant, shampoo, hair care product, hair conditioner, hair colorant, hair styling product and preferably take the form of an emulsion, lotion, milk, fluid, cream, hydrodispersion gel, balm, spray, alcoholic or aqueous/alcoholic solution, foam, powder, liquid soap, soap bar, shampoo, roll-on, stick or makeup. In hair treatment products the use is preferably directed towards the scalp or intracutaneosebaceous hair system.

It has also been found that a blackberry leaf extract according to the invention and oral care products containing this extract in an adequate concentration to inhibit MMP activity act against periodontitis and caries and in particular prevent it and delay its development. The use of blackberry leaf extract and corresponding oral care products advantageously anywhere in oral care or oral hygiene where desired effects are linked to MMP inhibition is therefore taught according to the invention. The extract or the oral care product is preferably used, however, as an active ingredient to prevent or slow down periodontitis and the excessive degradation of periodontal connective tissue and of MMP-related damage to the teeth, such as caries and erosions. To this end it is preferably brought into contact externally with the oral mucosa and the teeth. Such extracts and oral care formulations can be used according to the invention in particular to cleanse and care for the tooth substance and oral cavity and to freshen the breath.

The concentration of blackberry leaf extract (in liquid and/or concentrated form) in cosmetic (especially for topical application), oral hygiene and/or pharmaceutical preparations is preferably in the range from 0.00001 to 20 wt. %, preferably in the range from 0.0001 to 5 wt. % and particularly preferably in the range from 0.001 to 5 wt. %, relative to the total preparation.

The blackberry leaf extract used according to the invention can be incorporated without difficulty into common cosmetic or dermatological formulations such as pump sprays, aerosol sprays, creams, ointments, tinctures, lotions, nail care products and the like. It is also possible and in some cases advantageous here to combine the blackberry leaf extract used according to the invention with other active ingredients, for example with other active ingredients against skin ageing and wrinkles. The cosmetic and/or dermatological formulations containing blackberry leaf extract can otherwise have a conventional composition and be used to treat the skin and/or hair in the sense of a dermatological treatment or a treatment in the sense of conditioning cosmetics. They can also be used in makeup products in decorative cosmetics, however.

Preparations according to the invention containing a blackberry leaf extract according to the invention can also contain other MMP-inhibiting active ingredients and combinations of active ingredients, particularly against skin ageing and wrinkles or periodontitis and caries. All suitable or common active ingredients for oral hygiene, cosmetic and/or dermatological applications can be used here according to the invention. Particularly preferred here are soya protein or protein hydrolysates, soya isoflavones, hydrolysed rice protein, hydrolysed hazelnut protein, wheat protein, β-glucanes e.g. from oats and derivatives thereof, glycoproteins, ursolic acid and salts thereof, betulin, betulinic acid and salts thereof, retinol, retinol palmitate, epigallocatechin gallate, metastat, batimastat, chlorhexidine, propyl gallate, precocene, 6-hydroxy-7-methoxy-2,2-dimethyl-1(2H)-benzopyran, 3,4-dihydro-6-hydroxy-7-methoxy-2,2-dimethyl-1(2H)-benzopyran, creatine or other synthetic or natural MMP-inhibiting active ingredients, wherein the latter can also be used in the form of an extract from plants, such as e.g. green tea, *Sanguisorba officinalis, Centella asiatica, Ribes nigrum, Passiflora incarnata, Phyllanthus emblica, Filipendula ulmaria*, evening primrose, pomegranate, lady's mantle, rosemary, sage, echinacea, birch, apple, elm or soya.

Particularly preferred for use as additional active ingredients against skin ageing are β-glucane, 1,3-1,4-coupled β-glucane from oats being especially preferred, or wheat protein.

For use, the cosmetically and/or dermatologically active blackberry leaf extract is applied to the skin and/or the hair in an adequate amount in the conventional way for cosmetics and dermatological products. Cosmetic and dermatological preparations which contain an extract according to the invention and also act as sunscreens offer particular advantages here. These preparations advantageously contain at least one UVA filter and/or at least one UVB filter and/or at least one inorganic pigment. The preparations can be in various forms, such as are conventionally used for sunscreen preparations, for example. Thus for example they can form a solution, a water-in-oil (W/O) or oil-in-water (O/W) emulsion, or a multiple emulsion, of the water-in-oil-in-water (W/O/W) type for example, a gel, a hydrodispersion, a solid stick or an aerosol.

As mentioned, preparations containing blackberry leaf extract can particularly advantageously be combined with substances which absorb or reflect UV radiation, in particular for cosmetic or skin protection purposes (in other words not for oral hygiene purposes), the total amount of filter substances being from 0.01 wt. % to 40 wt. %, preferably 0.1% to 10 wt. %, in particular 1.0 to 5.0 wt. %, relative to the total weight of the preparations, in order to provide cosmetic preparations which protect the hair or skin from ultraviolet radiation. These preparations advantageously contain at least one UVA filter and/or at least one UVB filter and/or at least one inorganic pigment, such that a light protection factor of at least >2 (preferably >5) is obtained. These preparations according to the invention can be in various forms, such as are conventionally used for sunscreen preparations, for example. Thus for example they can be a solution, a water-in-oil (W/O) or oil-in-water (O/W) emulsion, or a multiple emulsion, of the water-in-oil-in-water (W/O/W) type for example, a gel, a hydrodispersion, a solid stick or an aerosol.

Advantageous UV filters are, for example: p-aminobenzoic acid, p-aminobenzoic acid ethyl ester (25 mol) ethoxylated, p-dimethylaminobenzoic acid-2-ethylhexyl ester, p-aminobenzoic acid ethyl ester (2 mol) N-propoxylated, p-aminobenzoic acid glycerol ester, salicylic acid homomenthyl ester (homosalates) (Neo Heliopan®HMS), salicylic acid-2-ethylhexyl ester (Neo Heliopan®OS), triethanolamine salicylate, 4-isopropyl benzyl salicylate, anthranilic acid menthyl ester (Neo Heliopan®MA), diisopropyl cinnamic acid ethyl ester, p-methoxycinnamic acid-2-ethylhexyl ester (Neo Heliopan®AV), diisopropyl cinnamic acid methyl ester, p-methoxycinnamic acid isoamyl ester (Neo Heliopan®E 1000), p-methoxycinnamic acid diethanolamine salt, p-methoxycinnamic acid isopropyl ester, 2-ethylhexyl-2-cyano-3,3-diphenyl acrylate (Neo Heliopan®303), ethyl-2-cyano-3,3'-diphenyl acrylate, 2-phenyl benzimidazole sulfonic acid and salts (Neo Heliopan®Hydro), 3-(4'-trimethyl ammonium) benzylidene bornan-2-one methyl sulfate, terephthalylidene dibornane sulfonic acid and salts (Mexoryl®SX), 4-t-butyl-4'-methoxydibenzoyl methane (avobenzone)/(Neo Heliopan®357), ß-imidazole-4(5)-acrylic acid (urocanic acid), 2-hydroxy-4-methoxybenzophenone (Neo Heliopan®BB), 2-hydroxy-4-methoxybenzophenone-5-sulfonic acid, dihydroxy-4-methoxybenzophenone, 2,4-dihydroxybenzophenone, tetrahydroxybenzophenone, 2,2'-dihydroxy-4,4'-dimethoxybenzophenone, 2-hydroxy-4-n-octoxybenzophenone, 2-hydroxy-4-methoxy-4'-methyl benzophenone, 3-(4'-sulfo)benzylidene bornan-2-one and salts, 3-(4'-methyl benzylidene)-d,l-camphor (Neo Heliopan®MBC), 3-benzylidene-d,l-camphor, 4-isopropyl dibenzoyl methane, 2,4,6-trianilino-(p-carbo-2'-ethylhexyl-1-oxy)-1,3,5-triazine, phenylene bis-benzimidazyl tetrasulfonic acid disodium salt (Neo Heliopan®AP), 2,2'-(1,4-phenylene)-bis-(1H-benzimidazole-4,6-disulfonic acid), monosodium salt, N-[(2 and 4)-[2-(oxoborn-3-ylidene)

methyl]benzyl] acrylamide polymer, phenol, -(2H-benzotriazol-2-yl)-4-methyl-6-(2-methyl-3(1,3,3,3-tetramethyl-1-(trimethylsilyl)oxy)disiloxyanyl)propyl), (Mexoryl®XL), 4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb®HEB), 2,2'-methylene bis-(6-(2H-benzotriazol-2-yl)-4-1,1,3,3-tetramethylbutyl) phenol) (Tinosorb®M), 2,4-bis-[4-(2-ethylhexyloxy)-2-hydroxyphenyl]-1,3,5-triazine, benzylidene malonate polysiloxane (Parsol®SLX), glyceryl ethyl hexanoate dimethoxycinnamate, disodium-2,2'-dihydroxy-4,4'-dimethoxy-5,5'-disulfobenzophenone, dipropylene glycol salicylate, sodium hydroxymethoxybenzophenone sulfonate, 4,4',4-(1,3,5-triazine-2,4,6-triyltriimino) tris-benzoic acid tris(2-ethylhexyl ester) (Uvinul®T150), 2,4-bis-[{(4-(2-ethylhexyloxy)-2-hydroxy} phenyl]-6-(4-methoxyphenyl)-1,3,5-triazine (Tinosorb®S), 2,4-bis-[{(4-(3-sulfonato)-2-hydroxypropyloxy)-2-hydroxy} phenyl]-6-(4-methoxyphenyl)-1,3,5-triazine sodium salt, 2,4-bis-[{(3-(2-propyloxy)-2-hydroxypropyloxy)-2-hydroxy} phenyl]-6-(4-methoxyphenyl)-1,3,5-triazine, 2,4-bis-[{4-(2-ethylhexyloxy)-2-hydroxy} phenyl]-6-[4-(2-methoxyethyl carbonyl) phenylamino]-1,3,5-triazine, 2,4-bis-[{4-(3-(2-propyloxy)-2-hydroxypropyloxy)-2-hydroxy} phenyl]-6-[4-(2-ethylcarboxyl) phenylamino]-1,3,5-triazine, 2,4-bis-[{4-(2-ethylhexyloxy)-2-hydroxy} phenyl]-6-(1-methyl pyrrol-2-yl)-1,3,5-triazine, 2,4-bis-[{4-tris-(trimethylsiloxysilyl propyloxy)-2-hydroxy} phenyl]-6-(4-methoxyphenyl)-1,3,5-triazine, 2,4-bis-[{4-(2"-methylpropenyloxy)-2-hydroxy} phenyl]-6-(4-methoxyphenyl)-1,3,5-triazine, 2,4-bis-[{4-(1',1',1',3'5',5', 5'-heptamethylsiloxy-2"-methylpropyloxy)-2-hydroxy} phenyl]-6-(4-methoxyphenyl)-1,3,5-triazine, 2-(4-diethylamino-2-hydroxybenzoyl) benzoic acid hexylester (Uvinul® A Plus), indanylidene compounds in accordance with DE 100 55 940 (=WO 02/38537).

UV absorbers that are particularly suitable for combining are p-aminobenzoic acid, 3-(4'-trimethyl ammonium) benzylidene bornan-2-one methyl sulfate, salicylic acid homomenthyl ester (Neo Heliopan®HMS), 2-hydroxy-4-methoxybenzophenone (Neo Heliopan®BB), 2-phenyl benzimidazole sulfonic acid (Neo Heliopan®Hydro), terephthalylidene dibornane sulfonic acid and salts (Mexoryl®SX), 4-tert.-butyl-4'-methoxydibenzoyl methane (Neo Heliopan®357), 3-(4'-sulfo)benzylidene bornan-2-one and salts, 2-ethylhexyl-2-cyano-3,3-diphenyl acrylate (Neo Heliopan®303), N-[(2 and 4)-[2-(oxoborn-3-ylidene) methyl]benzyl]-acrylamide polymer, p-methoxycinnamic acid-2-ethylhexyl ester (Neo Heliopan®AV), p-aminobenzoic acid ethyl ester (25 mol) ethoxylated, p-methoxycinnamic acid isoamyl ester (Neo Heliopan®E1000), 2,4,6-trianilino-(p-carbo-2'-ethylhexyl-1'-oxy)-1,3,5-triazine (Uvinul®T150), phenol, 2-(2H-benzotriazol-2-yl)-4-methyl-6-(2-methyl-3(1,3,3,3-tetramethyl-1-(trimethylsilyl)-oxy)disiloxyanyl)propyl), (Mexoryl®XL), 4,4'-[(6-[4-(1,1-dimethyl) aminocarbonyl)-phenylamino]-1,3,5-triazine-2,4-diyl) diimino]-bis-(benzoic acid-2-ethylhexyl ester), (Uvasorb®HEB), 3-(4'-methylbenzylidene)-d,l-camphor (Neo Heliopan®MBC), 3-benzylidene camphor, salicylic acid-2-ethylhexyl ester (Neo Heliopan®OS), 4-d imethylaminobenzoic acid-2-ethylhexyl ester (Padimate O), hydroxy-4-methoxybenzophenone-5-sulfonic acid and Na salt, 2,2'-methylene bis-(6-(2H-benzotriazol-2-yl)-4-1,1,3,3-tetramethylbutyl) phenol) (Tinosorb®M), phenylene bis-benzimidazyl tetrasulfonic acid disodium salt (Neo Heliopan®AP), 2,4-bis-[{(4-(2-ethylhexyloxy)-2-hydroxy} phenyl]-6-(4-methoxyphenyl)-1,3,5-triazine (Tinosorb®S), benzylidene malonate polysiloxane (Parsol®SLX), menthyl anthranilate (Neo Heliopan®MA), 2-(4-diethylamino-2-hydroxybenzoyl)-benzoic acid hexyl ester (Uvinul® A Plus), indanylidene compounds in accordance with DE 100 55 940 (=WO 02/38537).

Advantageous inorganic light protection pigments are finely dispersed metal oxides and metal salts, for example titanium dioxides, zinc oxide (ZnO), iron oxides (e.g. $Fe_2O_3$), aluminium oxide ($Al_2O_3$); cerium oxides (e.g. $Ce_2O_3$), manganese oxides (e.g. MnO), zirconium oxide ($ZrO_2$), silicon oxide ($SiO_2$) silicates (talc), mixed oxides of the corresponding metals and mixtures of such oxides, barium sulfate and zinc stearate. Pigments based on $TiO_2$ or zinc oxide are particularly preferred. In preferred embodiments the particles have an average diameter of less than 100 nm, preferably between 5 and 50 nm and particularly preferably between 15 and 30 nm. They can display a spherical form, but such particles having an ellipsoid form or other form deviating from the spherical shape can also be used. The pigments can also be surface treated, i.e. hydrophilised or hydrophobed. Typical examples are coated titanium dioxides, such as e.g. titanium dioxide T 805 (Degussa) or Eusolex® T2000 (Merck) or coated zinc oxide, such as e.g. zinc oxide NDM. Suitable hydrophobic coating agents are above all silicones and especially trialkoxyoctyl silanes or simethicones. So-called micro-pigments or nano-pigments are preferably used in sunscreens. Zinc micro- or nano-pigments are preferably used.

The total amount of inorganic pigments, particularly hydrophobic inorganic micro-pigments, in the finished cosmetic or dermatological formulations is advantageously in the range from 0.1 to 30 wt. %, preferably 0.1 to 10.0, in particular 0.5 to 6.0 wt. %, relative to the total weight of the formulations.

The blackberry leaf extract according to the invention can be incorporated into diverse pharmaceutical forms of oral hygiene products, without being tied down to one or a few specific pharmaceutical forms, since it harmonises advantageously with a very large number of conventional auxiliary substances and additives.

It is advantageous to buffer the oral hygiene products according to the invention. A pH range of 3.5 to 10.0 is particularly advantageous and preferred.

A blackberry leaf extract for use according to the invention for oral hygiene purposes can be incorporated without difficulty into common formulations for oral hygiene products. Preferred oral hygiene products are, for example, tooth creams, toothpastes, tooth gels, mouth washes, mouth rinses, gargle liquids and mouth or breath sprays, as well as lozenges, pastilles, sweets, chewing gums, chew sweets and dental care chewing gums.

It is also possible and mostly advantageous for oral hygiene purposes to combine a blackberry leaf extract according to the invention with other ingredients, for example with antimicrobially active or anti-inflammatory substances, aromatic substances, flavourings and/or auxiliary substances.

The oral hygiene products according to the invention can contain auxiliary substances such as are conventionally used in such preparations, for example preservatives, abrasives, antibacterial agents, anti-inflammatory agents, irritation-preventing agents, irritation-inhibiting agents, antimicrobial agents, antioxidants, astringents, antiseptic agents, antistatics, binders, buffers, support materials, chelating agents, cell stimulants, cleansing agents, conditioning agents, surface-active substances, deodorising agents, softeners, bactericides, emulsifiers, enzymes, ethereal oils, film formers, fixers, foaming agents, foam stabilisers, substances to prevent foaming, foam boosters, gelling agents, gel-forming agents, moisture-releasing agents, moisturising substances, moisture-retaining substances, bleaching agents, optical brighteners, dirt-repelling agents, friction-reducing agents, lubricants, opacifiers, concealing agents, brighteners, polymers, powders, proteins, polishing agents, silicones, skin-calming agents, skin-cleansing agents, skin care agents, skin-healing agents, cooling agents, skin-cooling agents, warming agents, skin-warming agents, stabilisers, suspending agents, thickeners, vitamins, oils, waxes, fats, phospholipids, saturated fatty acids, mono- or polyunsaturated fatty acids, a-hydroxy acids, polyhydroxy fatty acids, liquefiers, dyes, colour-protecting agents, pigments, aromas, flavourings, perfumes or other conventional constituents of an oral hygiene formulation, such as alcohols, polyols, electrolytes, organic solvents, sweeteners, sugar substitutes, silicas, calcium carbonate, calcium hydrogen phosphate, aluminium oxide, fluorides, zinc, tin, potassium, sodium and strontium salts, pyrophosphates, hydrogen peroxide, hydroxyapatites.

If the oral hygiene product is a solution or lotion, the following can be used as solvents, for example: water or aqueous solutions, oils, such as triglycerides of decanoic or octanoic acid, or alcohols, diols or polyols having a low C number and ethers thereof, preferably ethanol, isopropanol, propylene glycol, glycerol, ethylene glycol. Mixtures of the aforementioned solvents can naturally also be used.

Examples of flavourings or aromas which can form part of an oral hygiene product according to the invention in addition to a blackberry leaf extract according to the invention can be found for example in K. Bauer, D. Garbe, H. Surburg, Common Fragrance and Flavor Materials, 4th ed., Wiley-VCH, Weinheim 2001 or in S. Arctander, Perfume and Flavor Chemicals, Vol. I and II, Montclair, N.J., 1969, self-published.

Examples of natural aromas which can be cited which can form part of an oral hygiene product according to the invention in addition to a blackberry leaf extract according to the invention are: peppermint oils, spearmint oils, mentha arvensis oils, aniseed oils, clove oils, citrus oils, camphor oils, cinnamon oils, cinnamon bark oils, wintergreen oils, eucalyptus oils, eucalyptus citriodora oils, fennel oils, ginger oils, camomile oils, caraway oils, citronella oils, limette oils, orange oils, bergamot oils, grapefruit oils, mandarin oil, rose oils, geranium oils, sage oils, parsley seed oils, yarrow oils, star anise oils, basil oil, bitter almond oils, thyme oils, juniper berry oils, rosemary oils, angelica root oils, vanilla extracts, as well as fractions thereof and ingredients isolated therefrom.

Examples of homogeneous aromatic substances which can be cited which can form part of an oral hygiene product according to the invention in addition to a blackberry leaf extract according to the invention are: anethol, menthol, menthone, isomenthone, menthyl acetate, menthyl propionate, menthofuran, mintlactone, eucalyptol (1,8-cineol), limonene, eugenol, thymol, pinene, sabinene hydrate, 3-octanol, carvone, gamma-octalactone, gamma-nonalactone, germacrene-D, viridiflorol, 1,3E,5Z-undecatriene, isopulegol, piperitone, 2-butanone, ethyl formate, 3-octyl acetate, isoamyl isovalerianate, hexanol, hexanal, cis-3-hexenol, linalool, alpha-terpineol, cis- and trans-carvyl acetate, p-cymol, damascenone, damascone, rose oxide, fenchol, acetaldehyde diethylacetal, 1-ethoxyethyl acetate, cis-4-heptenal, isobutyraldehyde, isovaleraldehyde, cis-jasmone, methyl dihydrojasmonate, anisaldehyde, methyl salicylate, 2'-hydroxypropiophenone, menthyl methyl ether, myrtenyl acetate, 2-phenylethyl alcohol, 2-phenylethyl isobutyrate, 2-phenylethyl isovalerate, cinnamaldehyde, geraniol, nerol. In the case of chiral compounds the aromatic substances can take the form of a racemate or a single enantiomer or an enantiomer-concentrated mixture.

Advantageous aromas or aromatic substances which can form part of an oral hygiene product according to the invention in addition to a blackberry leaf extract according to the invention are, for example, aniseed oil, basil oil, bitter almond oil, camphor oil, citronella oil, citrus oils, eucalyptus citriodora oil, eucalyptus oil, camomile oil, spearmint oil, limette oil, mandarin oil, clove oil, orange oil, peppermint oil, sage oil, thyme oil, wintergreen oil, cinnamon oil, cinnamon bark oil, l-menthol, menthone, 1,8-cineol (eucalyptol), carvone, alpha-terpineol, methyl salicylate, Z-hydroxypropiophenone, menthyl methyl ether.

Compounds having a physiological cooling effect (cooling substances) which can form part of an oral hygiene product according to the invention and/or a cosmetic, dermatological and/or pharmaceutical product according to the invention in addition to a blackberry leaf extract according to the invention are, for example, l-menthol, menthone glycerol acetal, menthyl lactate, substituted menthyl-3-carboxylic acid amides (e.g. menthyl-3-carboxylic acid-N-ethylamide), 2-isopropyl-N,2,3-trimethyl butanamide, substituted cyclohexane carboxylic acid amides, 3-menthoxypropane-1,2-diol, 2-hydroxyethyl menthyl carbonate, 2-hydroxypropyl menthyl carbonate, N-acetyl glycine menthyl ester, menthyl hydroxycarboxylic acid esters (e.g. menthyl-3-hydroxybutyrate), monomenthyl succinate 2-mercaptocyclodecanone, menthyl-2-pyrrolidin-5-one carboxylate, 2,3-dihydroxy-p-menthane, 3,3,5-trimethyl cyctohexanone glycerol ketal, 3-menthyl-3,6-di- and tri-oxaalkanoates, 3-menthyl methoxyacetate, icilin, l-menthyl methyl ether. l-Menthol, menthone glycerol acetal, menthyl lactate, menthyl-3-carboxylic acid-N-ethylamide, 3-menthoxypropane-1,2-diol, 2-hydroxyethyl menthyl carbonate, 2-hydroxypropyl menthyl carbonate, monomenthyl succinate, menthyl-2-pyrrolidin-5-one carboxylate, 1-menthyl methyl ether are preferred.

Oral hygiene products which in addition to l-menthol contain at least one, particularly preferably at least two further cooling substances are preferred according to the invention.

Constituents which bring about a sensation of heat, sharpness, itching or prickling on the skin or on the mucous membranes, in particular aromatic substances having a heat-generating effect and/or compounds having a pungent taste (pungent principles), which can form part of an oral hygiene product and/or cosmetic, dermatological or pharmaceutical product according to the invention in addition to a blackberry leaf extract according to the invention are, for example, capsaicin, dihydrocapsaicin, gingerol, paradol, shogaol, piperine, paprika powder, chilli pepper powder, extracts of paprika, extracts of pepper; extracts of chilli pepper; extracts of ginger roots, extracts of *Aframomum melegueta*, extracts of *Spilanthes acmella*, extracts of *Kaempferia galanga*, extracts of *Alpinia galanga*, carboxylic acid-N-vanillylamides, in particular nonanoic acid-N-vanillylamide, 2-nonenoic acid amides, in particular 2-nonenoic acid-N-isobutylamide, 2-nonenoic acid-N-4-hydroxy-3-methoxyphenylamide, alkyl ethers of 4-hydroxy-3-methoxybenzyl alcohol, in particular 4-hydroxy-3-methoxybenzyl-n-butyl ether, alkyl ethers of 3-hydroxy-4-methoxybenzyl alcohol, alkyl ethers of 3,4-dimethoxybenzyl alcohol, alkyl ethers of 3-ethoxy-4-hydroxybenzyl alcohol, alkyl ethers of 3,4-methylene dioxybenzyl alcohol, (4-hydroxy-3-methoxyphenyl)acetic acid amides, in particular (4-hydroxy-3-methoxyphenyl)

acetic acid-N-n-octylamide, nicotinaldehyde, methyl nicotinate, propyl nicotinate, 2-butoxyethyl nicotinate, benzyl nicotinate, 1-acetoxychavicol.

Other constituents which can form part of an oral hygiene product according to the invention in addition to a blackberry leaf extract according to the invention are, for example, substances to improve oral hygiene, such as dental care and/or refreshing substances, for example. Substances to improve oral hygiene include, for example, substances to combat or prevent plaque, tartar or caries and those to combat or prevent bad breath. Reference is made in this connection to U.S. Pat. No. 5,043,154. Substances which can be cited by way of example are Zn salts, such as Zn citrate, Zn fluoride, Sn salts, such as Sn fluorides, Cu salts, fluorides, e.g. amine fluorides, alkali fluorides such as Na fluoride, alkaline-earth fluorides, ammonium fluoride, phosphates, pyrophosphates, fluorophosphates, such as Na monofluorophosphate, Al mono- and Al difluorophosphate, alpha-ionones, geraniol, thymol, isomenthyl acetate, panthenol (provitamin B5), xylitol, allantoin, niacinamide (vitamin B3), tocopheryl acetate (vitamin E actetate), poloxamer.

An oral hygiene product according to the invention can also contain in addition to a blackberry leaf extract according to the invention one or more antimicrobial active ingredients to improve oral hygiene. These active ingredients can be of a hydrophilic, amphoteric or hydrophobic nature. Examples of such active ingredients are: triclosan, chlorhexidine and salts thereof (e.g. chlorhexidine acetate, gluconate or hydrochloride), peroxides, phenols and salts thereof, domiphen bromide (phenododecinium bromide), bromochlorophene, Zn salts, chlorophylls, Cu salts, Cu gluconate, Cu chlorophyll, sodium lauryl sulfate, quaternary monoammonium salts such as cocoalkyl benzyl dimethyl ammonium chloride or pyridinium salts such as cetyl pyridinium chloride. In addition to individual active ingredients, mixtures of active ingredients or natural extracts or fractions thereof containing active ingredients can be used, such as those obtainable from neem, berberis, fennel, green tea, marigold, camomile, rosemary, thyme, propolis or turmeric, for example.

A cosmetic, dermatological or pharmaceutical product and/or oral hygiene product according to the invention can also contain, in addition to a blackberry leaf extract according to the invention, dyes, colorants or pigments, for example: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine yellow, bixin, norbixin (annatto, orlean), capsanthin, capsorubin, lycopene, beta-apo-8'-carotenal, beta-apo-8'-carotenic acid ethyl ester, xantophylls (flavoxanthin, lutein, cryptoxanthin, rubixanthin, violaxanthin, rodoxanthin), fast carmine (carminic acid, cochineal), azorubin, cochineal red A (Ponceau 4 R), beetroot red, betanin, anthocyanins, amaranth, patent blue V, indigotine I (indigo carmine), chlorophylls, copper compounds of chlorophylls, acid brilliant green BS (lissamine green), brilliant black BN, vegetable carbon, titanium dioxide, iron oxides and hydroxides, calcium carbonate, aluminium, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocyanine green, fast acid violet R. Other, naturally obtained extracts (e.g. paprika extract, black carrot extract, red cabbage extract) can also be used for colouring purposes.

Cosmetic, oral hygiene and/or pharmaceutical preparations which contain a blackberry leaf extract according to the invention can particularly advantageously contain antioxidants, wherein all suitable or common antioxidants for oral hygiene, cosmetic and/or dermatological applications can be used. The antioxidants are advantageously selected from the group consisting of amino acids (e.g. glycine, histidine, tyrosine, tryptophane) and derivatives thereof, imidazoles (e.g. urocanic acid) and derivatives thereof, peptides such as D, L-carnosine, D-carnosine, L-carnosine and derivatives thereof (e.g. anserine), carotenoids, carotenes (e.g. α-carotene, ß-carotene, lycopene) and derivatives thereof, chlorogenic acid and derivatives thereof, lipoic acid and derivatives thereof (e.g. dihydrolipoic acid), aurothioglucose, propyl thiouracil and other thiols (e.g. thioredoxin, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and the salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very small compatible doses, also (metal) chelators, e.g. α-hydroxy fatty acids, palmitic acid, phytic acid, lactoferrin, α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate, ascorbyl glycosides such as e.g. 6-O-acyl-2-O-a-D-glucopyranosyl-L-ascorbic acid, 6-O-acyl-2-O-ß-D-glucopyranosyl-L-ascorbic acid, 2-O-a-D-glucopyranosyl-L-ascorbic acid or 2-O-ß-D-glucopyranosyl-L-ascorbic acid), tocopherols and derivatives thereof (e.g. vitamin E acetate), vitamin A and derivatives thereof (vitamin A palmitate) as well as coniferyl benzoate, rutic acid and derivatives thereof, a-glucosyl rutin, quercetin and derivatives thereof, rosemarinic acid, carnosol, carnosolic acid, resveratrol, caffeic acid and derivatives thereof, sinapic acid and derivatives thereof, ferulic acid and derivatives thereof, furfurylidene glucitol, curcuminoids, butyl hydroxytoluene, butyl hydroxyanisole, nordihydroguaiacic resin acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatives thereof (e.g. selenium methionine), stilbenes and derivatives thereof (e.g. stilbene oxide, trans-stilbene oxide) along with derivatives (salts, esters, ethers, sugars, nucleotides, nucleosides, peptides and lipids) of these cited active ingredients or extracts or fractions of plants having an antioxidant effect, such as e.g. green tea, rooibos, honeybush, grape, rosemary, sage, melissa, thyme, lavender, olive, oats, cocoa, ginkgo, ginseng, liquorice, honeysuckle, sophora, pueraria, pinus, citrus, *Phyllanthus emblica* or St. John's wort.

Preferred oral hygiene, cosmetic and/or pharmaceutical preparations containing a blackberry leaf extract according to the invention also contain one or more vitamins and/or vitamin precursors, wherein all suitable or common vitamins and vitamin precursors for cosmetic and/or dermatological applications can be used. These include in particular vitamins and vitamin precursors such as tocopherols, vitamin A, niacin and niacinamide, other B-complex vitamins, in particular biotin and vitamin C, panthenol and derivatives thereof, particularly the esters and ethers of panthenol and cationically derivatised panthenols such as e.g. panthenol triacetate, panthenol monoethyl ether and the monoacetate thereof as well as cationic panthenol derivatives. The following specific examples can be cited: vitamin A (retinol) and derivatives thereof (e.g. vitamin A acetate, vitamin A acid, vitamin A aldehyde, vitamin A palmitate, vitamin A propionate), vitamin B1 (thiamin) and salts thereof (e.g. vitamin B1 hydrochloride, vitamin B1 mononitrate, thiamin diphosphate, thiamin pyrophosphate), vitamin B12 (cobalamin), vitamin B2 (vitamin G, riboflavin) and derivatives thereof (e.g. vitamin B2 tetraacetates), vitamin B3 and derivatives thereof (e.g. nicotinamide ascorbate, nicotinamide glycolate, nicotinamide hydroxycitrate, nicotinamide lactate, nicotinamide malate, nicotinamide mandelate, nicotinamide salicylate, nicotinamide thioctate), vitamin B4 (adenine) and derivatives thereof (e.g. adenine riboside, disodium flavin adenine dinucleotide, nicotinamide adenine dinucleotide), provitamin B5, vitamin B5 (pantothenic acid) and derivatives thereof (e.g. acetyl pantothenyl ethyl ether, allantoin calcium pantothenate, allantoin DL-pantothenyl alcohol, bis(pantothenamidoethyl) disulfide, calcium pantothenate, hydroxyethyl pantothenamide MEA, sodium pantothenate, N-D-pantothenoyl-2-(2-aminoethoxy)ethanol, N-D-pantothenoyl-2-aminoethanol, N-hydroxyethoxyethyl pantothenamide, N-hydroxyethyl pantothenamides, pantothenamide MEA, pantothenol, pantothenic acid lactones, pantothenic acid polypeptide, pantothenyl ethyl ether), vitamin B6 (pyridoxol, pyroxidal, pyridoxamine) and derivatives thereof (e.g. pyridoxine dicaprylate, vitamin B6 dilaurates, vitamin B6 dioctanoates, vitamin B6 dipalmitates, pyridoxine glycyrrhetinate, vitamin B6 hydrochlorides, vitamin B6 phosphates, vitamin B6 serines, vitamin B6 tripalmitates), vitamin C (ascorbic acid) and derivatives thereof (e.g. 3-O-ethyl ascorbic acid, allantoin ascorbate, aminopropyl ascorbyl phosphate, araboascorbic acid, monosodium salt, ascorbic acid palmitate, ascorbic acid polypeptide, ascorbosilane C, ascorbyl dipalmitate, ascorbyl glucoside, ascorbyl inositol nicotinate, ascorbyl linoleate, ascorbyl methylsilanol pectinate, ascorbyl nicotinamide, ascorbyl phosphate magnesium, ascorbyl stearate, ascorbyl tetraisopalmitate, ascorbyl tocopheryl maleate, calcium ascorbate, chitosan ascorbate, D-arabino ascorbic acid, disodium ascorbyl sulfates, glucosamine ascorbate, inositol hexanicotinate hexaascorbate, isoascorbic acid, L-ascorbic acid, 2-(dihydrogen phosphate), trisodium salt, L-ascorbic acid, 2-[(3-cholest-5-en-3-yl hydrogen phosphate], monosodium salt, L-ascorbic acid, 2-O-D-glucopyranosyl, L-ascorbic acid, 3-O-ethyl ether, magnesium ascorbate, magnesium ascorbyl borate, methoxy PEG-7 ascorbic acid, methyl silanol ascorbate, potassium ascorbyl tocopheryl phosphate, potassium ascorbyl borates, sodium ascorbate, sodium ascorbyl phosphate, sodium ascorbyl/cholesteryl phosphate, sodium isoascorbate, sodium L-ascorbyl-2-phosphate, tetrahexyldecyl ascorbate), provitamin D, vitamin D (calciol) and derivatives thereof (e.g. vitamin D2, vitamin D3), vitamin E (D-alpha-tocopherol) and derivatives thereof (e.g. dl-alpha-tocopherol, polyoxypropylene/polyoxyethylene/tocopherol ether, polypropylene glycol/tocopherol ether, tocopherol cysteamine, tocopherol phosphate, sodium vitamin E phosphate, vitamin E acetate, vitamin E linoleates, vitamin E nicotinates, vitamin E succinates), vitamin F (essential fatty acids, linolenic acid and linoleic acid) and derivatives thereof (e.g. vitamin F ethyl ester, vitamin F glyceryl ester), vitamin H (vitamin B7, biotin), vitamin K1 (phylloquinones, phytonadiones) and vitamin K3 (menadiones, menaquinone).

A combination with (metal) chelators can also be advantageous in some preparations. (Metal) chelators which are preferably to be used here are α-hydroxy fatty acids, phytic acid, lactoferrin, α-hydroxy acids such as e.g. citric acid, lactic acid and malic acid as well as humic acids, bile acids, bile extracts, bilirubin, biliverdin and EDTA, EGTA and derivatives thereof.

Preferred cosmetic, pharmaceutical and/or oral hygiene preparations according to the invention containing a blackberry leaf extract according to the invention can also contain anti-inflammatory active ingredients and/or active ingredients to relieve reddening and/or itching. All anti-inflammatory active ingredients or active ingredients to relieve reddening and/or itching which are suitable for cosmetic and/or dermatological and/or oral hygiene applications can be used here. The following are advantageously used as anti-inflammatory active ingredients or as active ingredients to relieve reddening and/or itching: steroidal anti-inflammatory substances of the corticosteroid type, such as e.g. hydrocortisone, dexamethasone, dexamethasone phosphate, methyl prednisolone or cortisone or another steroidal anti-inflammatory. Non-steroidal anti-inflammatories can also be used, such as for example oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Alternatively, natural anti-inflammatory substances or substances to relieve reddening and/or itching can be used. Plant extracts, special highly active plant extract fractions and highly pure active substances isolated from plant extracts can be used.

Particularly preferred are extracts, fractions and active substances from camomile, aloe vera, commiphora species, rubia species, willow, willowherb, oats, calendula, arnica, St. John's wort, honeysuckle, rosemary, melissa, ginger, *Passiflora incarnata*, witch hazel, pueraria, avena, dianthus and echinacea as well as pure substances such as inter alia bisabolol, apigenin, apigenin-7-glucoside, rosemarinic acid, boswellic acid, phytosterols, glycyrrhizinic acid, glabridin, licochalcone A. The formulations containing blackberry leaf extract can also contain mixtures of two or more anti-inflammatory active ingredients.

Particularly preferred for cosmetic, pharmaceutical and dermatological and/or oral hygiene use within the meaning of the invention are bisabolol, boswellic acid, and extracts and isolated highly pure active ingredients obtained from oats and echinacea, α-bisabolol and extracts and isolated highly pure active ingredients obtained from oats being preferred in particular.

The amount of anti-irritants (one or more compounds) in the preparations according to the invention is preferably 0.0001 to 20 wt. %, particularly preferably 0.0001 to 10 wt. %, in particular 0.001 to 5 wt. %, relative to the total weight of the preparation.

Blackberry leaf extract can advantageously be used for cosmetic and/or dermatological purposes in combination with skin-lightening active ingredients. All suitable or common skin-lightening active ingredients for cosmetic and/or dermatological applications can be used here according to the invention. Advantageous skin-lightening active ingredients in this respect are kojic acid (5-hydroxy-2-hydroxymethyl-4-pyranone), kojic acid derivatives e.g. kojic acid dipalmitate, arbutin, ascorbic acid, ascorbic acid derivatives, hydroquinone, hydroquinone derivatives, resorcinol, sulfur-containing molecules such as e.g. glutathione or cysteine alpha-hydroxy acids (e.g. citric acid, lactic acid, malic acid) and derivatives thereof, chromone derivatives such as aloesin, N-acetyl tyrosine and derivatives, undecenoyl phenylalanine, gluconic acid, 4-alkyl resorcinols, vinyl and ethyl guiacol, inhibitors of nitrogen oxide synthesis, such as e.g. L-nitroarginine and derivatives thereof, 2,7-dinitroindazole or thiocitrulline, metal chelators (e.g. a-hydroxy fatty acids, palmitic acid, phytic acid, lactoferrin, humic acid, bile acid, bile extracts, bilirubin, biliverdin, EDTA, EGTA and derivatives thereof), triterpenes such as lupeol or maslinic acid, flavonoids, retinoids, soya milk, serine protease inhibitors or lipoic acid or other synthetic or natural active ingredients for skin and hair lightening, wherein the latter can also be used in the form of an extract from plants, such as e.g. bearberry extract, rice extract, liquorice root extract or constituents concentrated therefrom, such as glabridin or licochalcone A, artocarpus extract, extract from rumex and ramulus species, extracts from pine species (pinus) and extracts from vitis species or stilbene derivatives concentrated therefrom, extract of saxifrage, mulberry, scutelleria or/and grapes.

The formulations according to the invention can preferably also contain other active ingredients which stimulate skin and hair tinting or lightening by chemical or natural means. A more rapid action based on synergistic effects is achieved in this way. Particularly preferred here are substrates or substrate analogues of tyrosinase such as L-tyrosine, L-DOPA or L-dihydroxyphenylalanine, stimulators of tyrosinase activity or expression such as theophylline, caffeine, proopiomelanocortin peptides such as ACTH, alpha-MSH, peptide analogues thereof and other substances which bind to the melanocortin receptor, purines, pyrimidines, folic acid, phenylalanine derivatives such as e.g. undecylenoyl phenylalanine, diacylglycerols, aliphatic or cyclic diols, psoralens, prostaglandins and analogues thereof, activators of adenylate cyclase and compounds which activate the transfer of melanosomes into keratinocytes such as serine proteases or agonists of the PAR-2 receptor, extracts of plants and plant parts of the chrysanthemum species, walnut extracts, erythrulose and dihydroxyacetone.

Blackberry leaf extract can advantageously be used in cosmetic and dermatological preparations in particular in combination with insect repellents such as e.g. DEET, IR 3225, Dragorepel (Symrise GmbH & Co. KG).

Blackberry leaf extract can furthermore be advantageously used in cosmetic and dermatological preparations in particular in combination with hair growth inhibitors such as, for example, soya milk, soya protein, soya protein hydrolysate or extracts of plants and plant parts from *Sanguisorba officinalis, Calendula officinalis, Hamamelis virginiana, Arnica montana, Salix alba, Hypericum perforatum, Chondrus* species, *Gloiopeltis* species, *Ceramium* species, *Durvillea* species, plants of the leguminosae family, solanaceae, graminae or cucurbitaceae.

In numerous cases blackberry leaf extract can advantageously also be used in combination with osmolytes, in particular quaternary amines, amino acids and polyols. Preferred osmolytes are, furthermore: substances from the group of sugar alcohols (myo-inositol, mannitol, sorbitol), taurin, choline, betaine, betaine glycine, ectoine, diglycerol phosphate, phosphorylcholine, glycerophosphorylcholines, glutamine, glycine, alanine, glutamate, aspartate or proline, phosphatidylcholine, phosphatidylinositol, inorganic phosphates, proteins, peptides, polyamine acids and polyols. In cosmetic and dermatological applications it is advantageous here for the cited osmolytes also to have skin-moistening properties.

Blackberry leaf extract can advantageously be used in cosmetic and dermatological preparations in particular in combination with hair care agents and anti-dandruff active ingredients (e.g. climbazole, ketoconazole, piroctone oleamine, zinc pyrithione).

Blackberry leaf extract according to the invention can also advantageously be used in many cases in combination with one or more preservatives in preparations according to the invention. Preservatives such as benzoic acid, esters and salts thereof, propionic acid and salts thereof, salicylic acid and salts thereof, 2,4-hexadienoic acid (sorbic acid) and salts thereof, formaldehyde and paraformaldehyde, 2-hydroxybiphenyl ether and salts thereof, 2-zinc sulfid-opyridine-N-oxide, inorganic sulfites and bisulfites, sodium iodate, chlorobutanol, 4-ethyl mercury(II)-5-amino-1,3-bis(2-hydroxybenzoic acid, salts and esters thereof, dehydracetic acid, formic acid, 1,6-bis(4-amidino-2-bromophenoxy)-n-hexane and salts thereof, the sodium salt of ethyl mercury (II)-thiosalicylic acid, phenyl mercury and salts thereof, 10-undecenoic acid and salts thereof, 5-amino-1,3-bis(2-ethylhexyl)-5-methyl-hexahydropyrimidine, 5-bromo-5-nitro-1,3-dioxan, 2-bromo-2-nitro-1,3-propanediol, 2,4-dichlorobenzyl alcohol, N-(4-chlorophenyl)-N'-(3,4-dichlorophenyl) urea, 4-chloro-m-cresol, 2,4,4'-trichloro-2'-hydroxydiphenyl ether, 4-chloro-3,5-dimethyl phenol, 1,1'-methylene-bis(3-(1-hydroxymethyl-2,4-dioximidazolidin-5-yl)urea), poly(hexamethylene diguanide)hydrochloride, 2-phenoxyethanol, hexamethylene tetramine, 1-(3-chloroallyl)-3,5,7-triaza-1-azoniaadamantane chloride, 1-(4-chlorophenoxy)-1-(1H-imidazol-1-yl)-3,3-dimethyl-2-butanone, 1,3-bis-(hydroxymethyl)-5,5-dimethyl-2,4-imidazolidin-edione, benzyl alcohol, octopirox, 1,2-dibromo-2,4-dicyanobutane, 2,2'-methylene-bis(6-bromo-4-chlorophenol), bromochiorophene, mixture of 5-chloro-2-methyl-3(2H)-isothiazolinone and 2-methyl-3(2H)-iso-thiazolinone with magnesium chloride and magnesium nitrate, 2-benzyl-4-chloro-phenol, 2-chloroacetamide, chlorhexidine, chlorhexidine acetate, chlorhexidine gluconate, chlorhexidine hydrochloride, 1-phenoxypropan-2-ol, N-alkyl-($C_{12}$-$C_{22}$)-trimethyl-ammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethyl urea, 1,6-bis(4-amidinophenoxy)-n-hexane and salts thereof, glutaraldehyde, 5-ethyl-1-aza-3,7-dioxabicyclo(3.3.0)octane, 3-(4-chlorophenoxy)-1,2-propanediol, hyamine, alkyl-($C_8$-$C_{18}$)-dimethylbenzyl ammonium chloride, alkyl-($C_8$-$C_{18}$)-dimethylbenzyl ammonium bromide, alkyl-($C_8$-$C_{18}$)-dimethylbenzyl ammonium saccharinate, benzyl hemiformal, 3-iodine-2-propinyl butyl carbamate, sodium hydroxymethylamino acetate or sodium hydroxymethylamino acetate are preferably chosen here.

It is also preferable according to the invention to use blackberry leaf extract in combination with substances which are principally used to inhibit the growth of undesirable micro-organisms on or in animal organisms. Worth mentioning in this respect in addition to standard preservatives as further active ingredients are in particular, in addition to the large group of standard antibiotics, the products relevant for cosmetics, such as triclosan, climbazole, octoxyglycerol, octopirox (1-hydroxy-4-methyl-6-(2,4,4-trimethylpentyl)-2(1H)-pyridones, 2-aminoethanol), chitosan, farnesol, glycerol monolaurate, 1,2-decanediol or combinations of the cited substances, which are used inter alia against underarm odour, foot odour or dandruff formation.

Blackberry leaf extract can moreover also be used especially advantageously according to the invention in combination with perspiration-inhibiting active ingredients (antiperspirants) in cosmetic, dermatological and/or pharmaceutical preparations to combat body odour. Aluminium salts such as aluminium chloride, aluminium chlorohydrate, nitrate, sulfate, acetate, etc. are used above all as perspiration-inhibiting active ingredients. The use of zinc, magnesium and zirconium compounds can also be advantageous, however. For use in cosmetic and dermatological antiperspirants the aluminium salts and—to a somewhat lesser extent—aluminium/zirconium salt combinations have proved themselves in the main. Also worth mentioning are the partially neutralised and hence more compatible with the skin, but not quite so effective, aluminium hydroxychlorides. Other possible substances in addition to aluminium salts are for example a) protein-precipitating substances such as inter alia formaldehyde, glutaraldehyde, natural and synthetic tannins and trichloroacetic acid, which bring about a surface closure of the sweat glands, b) local anaesthetics (including dilute solutions of e.g. lidocaine, prilocaine or mixtures of such substances), which switch off the sympathic supply to the sweat glands by blocking the peripheral nerves, c) type X, A or Y zeolites which in addition to reducing sweat secretion also act as adsorbing agents for unpleasant odours, and d) botulinus toxin (toxin of the bacterium Chlostridium botulinum), which is also used for hyperhidrosis, a pathologically increased sweat secretion, and whose action is based on an irreversible blocking of the release of the transmitter substance acetyl choline which is relevant for sweat secretion.

Blackberry leaf extract can advantageously be combined in cosmetic and dermatological preparations with cosmetic auxiliary substances which are conventionally used in such preparations, in other words with, for example: perfume oils; antifoaming agents; dyes; pigments which have a colouring action; thickeners; surface-active substances; emulsifiers; softening substances; moistening and/or moisture-retaining substances; fats; oils; waxes; other conventional constituents of a cosmetic formulation such as alcohols, polyols, polymers, foam stabilisers, electrolytes, organic solvents or silicone derivatives.

In blackberry leaf extract-containing formulations for the topical prophylactic or cosmetic treatment of the skin, a high content of conditioning substances is usually advantageous. According to a preferred embodiment the compositions contain one or more conditioning animal and/or vegetable fats and oils such as olive oil, sunflower oil, refined soya oil, palm oil, sesame oil, rapeseed oil, almond oil, borage oil, evening primrose oil, coconut oil, shea butter, jojoba oil, sperm oil, beef fat, neatsfoot oil and pig fat and optionally other conditioning constituents such as for example fatty alcohols having 8 to 30 C atoms. The fatty alcohols here can be saturated or unsaturated and linear or branched. Examples that can be used include decanol, decenol, octanol, octenol, dodecanol, dodecenol, octadienol, decadienol, dodecadienol, oleyl alcohol, ricinol alcohol, erucic alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, as well as Guerbet alcohols thereof, wherein the list could be extended almost at will with other alcohols having a related chemical structure. The fatty alcohols preferably come from natural fatty acids, being conventionally produced from the corresponding esters of the fatty acids by reduction. Also usable are fatty alcohol fractions produced by reduction from naturally occurring fats and fatty oils, such as e.g. beef fat, groundnut oil, colza oil, cottonseed oil, soya bean oil, sunflower oil, palm kernel oil, linseed oil, maize oil, castor oil, rapeseed oil, sesame oil, cocoa butter and coconut butter.

Other conditioning substances which combine well according to the invention with blackberry leaf extract include Ceramides, wherein ceramides are understood to be N-acyl sphingosines (fatty acid amides of sphingosine) or synthetic analogues of such lipids (so-called pseudoceramides), which markedly improve the water-retaining capacity of the stratum corneum.

Phospholipids, for example soya lecithin, egg lecithin and kephalins

Vaseline, paraffin and silicone oils; the latter include inter alia dialkyl and alkylaryl siloxanes such as dimethyl polysiloxane and methylphenyl polysiloxane, as well as alkoxylated and quaternised derivatives thereof.

Animal and/or plant protein hydrolysates can advantageously also be added to the blackberry leaf extract. Advantageous in this respect are in particular elastin, collagen, keratin, milk protein, soya protein, oat protein, pea protein, almond protein and wheat protein fractions or corresponding protein hydrolysates, but also condensation products thereof with fatty acids and quaternised protein hydrolysates, the use of plant protein hydrolysates being preferred.

If a cosmetic or dermatological preparation containing blackberry leaf extract is a solution or lotion, the following can advantageously be used as solvents:

Water or aqueous solutions;

Fatty oils, fats, waxes and other natural and synthetic fat bodies, preferably esters of fatty acids with low C-number alcohols, for example with isopropanol, propylene glycol or glycerol, or esters of fatty alcohols with low C-number alkanoic acids or with fatty acids;

Alcohols, diols or polyols having a low C-number, as well as ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogue products. Mixtures of the aforementioned solvents are used in particular. In the case of alcoholic solvents, water can be an additional constituent.

Cosmetic preparations according to the invention containing blackberry leaf extract can advantageously also contain moisture regulators. The following substances, for example, can be used as moisture regulators (moisturisers): sodium lactate, urea, alcohols, sorbitol, glycerol, diols such as propylene glycol, 1,2-pentanediol, 1,2-hexanediol and 1,2-octanediol, collagen, elastin or hyaluronic acid, diacyl adipates, petroleum jelly, ectoine, urocanic acid, lecithin, pantheol, phytanetriol, lycopene, ceramides, cholesterol, glycolipids, chitosan, chondroitin sulfate, polyamino acids and sugars, lanolin, lanolin esters, amino acids, alphahydroxy acids (e.g. citric acid, lactic acid, malic acid) and derivatives thereof, sugars (e.g. inositol), alpha-hydroxy fatty acids, phytosterols, triterpene acids such as betulinic acid or ursolic acid, algal extracts.

In preferred embodiments of the invention cosmetic preparations containing blackberry leaf extract can also contain mono-, di- and oligosaccharides.

It is also preferable for cosmetic preparations containing blackberry leaf extract to contain one or more other plant extracts, which are conventionally produced by extraction of the entire plant, but also in individual cases exclusively from flowers and/or leaves, wood, bark or roots of the plant. With regard to the plant extracts for use for cosmetic, pharmaceutical and/or dermatological purposes, the person skilled in the art will take into account the ingredients listed in the table beginning on page 44 of the 3$^{rd}$ edition of the Leitfaden zur Inhaltsstoffdeklaration kosmetischer Mittel, published by the Industrieverband Körperpflegemittel and Waschmittel e.V. (IKW), Frankfurt. Particularly advantageous for cosmetic, dermatological, pharmaceutical and/or oral hygiene purposes are the extracts of aloe, witch hazel, algae, oak bark, willowherb, stinging nettle, dead-nettle, butcher's broom, hops, camomile, yarrow, arnica, calendula, burdock, horsetail, whitethorn, rose, lime blossom, liquorice, almond, pine, horse chestnut, sandalwood, juniper, coconut, mango, apricot, orange, lemon, limette, grapefruit, apple, strawberry, raspberry, grape, pomegranate, green tea, rooibos, honeybush, grapefruit seed, kiwi, avocado, cucumber, wheat, oats, barley, sage, thyme, wild thyme, lavender, rosemary, peppermint, melissa, birch, elder, olive, mallow, lady's smock, horsetail, willow bark, restharrow, coltsfoot, marshmallow, ginseng, ginkgo, pueraria, sophora, honeysuckle, angelica root, cinnamon, lemongrass and ginger root. The extracts from aloe vera, camomile, algae, rosemary, calendula, ginseng, cucumber, sage, stinging nettle, lime blossom, arnica and witch hazel are particularly preferred here. Mixtures of two or more plant extracts can also be used. Water, alcohols and mixtures thereof, inter alia, can be used as extractants to produce the cited plant extracts. Of the alcohols, low alcohols such as ethanol and isopropanol, but also polyhydric alcohols such as ethylene glycol, propylene glycol and butylene glycol, are preferred, both as the sole extractant and in blends with water. The plant extracts can be used in both pure and diluted form.

According to the invention, cosmetic preparations containing blackberry leaf extract can also contain, especially if crystalline or microcrystalline solids, for example inorganic micropigments, are to be incorporated into the preparations, anionic, cationic, non-ionic and/or amphoteric surfactants. Surfactants are amphiphilic substances, which can dissolve organic, non-polar substances in water. The hydrophilic components of a surfactant molecule are mostly polar functional groups, for example —COO_, —OSO$_3^{2-}$, —SO$_3^-$, whilst the hydrophobic components are generally non-polar hydrocarbon radicals. Surfactants are generally classified according to the type and charge of the hydrophilic molecule component. There are four different groups:
  anionic surfactants,
  cationic surfactants,
  amphoteric surfactants and
  non-ionic surfactants.

Anionic surfactants generally display carboxylate, sulfate or sulfonate groups as functional groups. In aqueous solution they form negatively charged organic ions in the acid or neutral environment. Cationic surfactants are almost exclusively characterised by the presence of a quaternary ammonium group. In aqueous solution they form positively charged organic ions in the acid or neutral environment. Amphoteric surfactants contain both anionic and cationic groups and therefore behave in aqueous solution in the same way as anionic or cationic surfactants, depending on the pH. They have a positive charge in a strongly acid environment and a negative charge in an alkaline environment. In the neutral pH range, by contrast, they are zwitterionic. Polyether chains are typical of non-ionic surfactants. Non-ionic surfactants do not form ions in the aqueous medium.

Anionic surfactants which can advantageously be used are acyl amino acids (and salts thereof), such as
  acyl glutamates, for example sodium acyl glutamate, di-TEA-palmitoyl aspartate and sodium caprylic/capric glutamate,
  acyl peptides, for example palmitoyl-hydrolysed milk protein, sodium cocoyl-hydrolysed soya protein and sodium/potassium cocoyl-hydroylsed collagen,
  sarcosinates, for example myristoyl sarcosin, TEA-lauroyl sarcosinate, sodium lauroyl sarcosinate and sodium cocoyl sarcosinate,
  taurates, for example sodium lauroyl taurate and sodium methyl cocoyl taurate,
  acyl lactylates, lauroyl lactylate, caproyl lactylate
  alaninates
carboxylic acids and derivatives, such as
  for example lauric acid, aluminium stearate, magnesium alkanolate and zinc undecylenate,
  ester carboxylic acids, for example calcium stearoyl lactylate, laureth-6 citrate and sodium PEG-4 lauramide carboxylate,
  ether carboxylic acids, for example sodium laureth-13 carboxylate and sodium PEG-6 cocamide carboxylate,
  phosphoric acid esters and salts, such as e.g. DEA-oleth-10-phosphate and dilaureth-4 phosphate,
  sulfonic acids and salts, such as
  acyl isothionates, e.g. sodium/ammonium cocoyl isethionate,
  alkyl aryl sulfonates,
  alkyl sulfonates, for example sodium cocomonoglyceride sulfate, sodium C$_{12-14}$ olefin sulfonate, sodium lauryl sulfoacetate and magnesium PEG-3 cocamide sulfate,
  sulfosuccinates, for example dioctyl sodium sulfosuccinate, disodium laureth sulfosuccinate, disodium lauryl sulfosuccinate and disodium undecylenamido MEA sulfosuccinate and
  sulfuric acid esters, such as
  alkyl ether sulfate, for example sodium, ammonium, magnesium, MIPA, TIPA laureth sulfate, sodium myreth sulfate and sodium C12-13 pareth sulfate,
  alkyl sulfates, for example sodium, ammonium and TEA lauryl sulfate.

Cationic surfactants which can advantageously be used are
  alkyl amines,
  alkyl imidazoles,
  ethoxylated amines and
  quaternary surfactants.

$$RNH_2CH_2CH_2COO^- \text{ (where pH=7)}$$

$$RNHCH_2CH_2COO\text{—}B^+ \text{ (where pH=12) } B^+=\text{any cation, e.g. Na}^+$$

esterquats

Quaternary surfactants contain at least one N atom, which is covalently bonded to 4 alkyl or aryl groups. This leads to a positive charge, regardless of the pH. Alkyl betaine, alkyl amidopropyl betaine and alkyl amidopropyl hydroxysulfaine are advantageous. The cationic surfactants used can also preferably be chosen from the group of quaternary ammonium compounds, in particular benzyl trialkyl ammonium chlorides or bromides, such as benzyl dimethylstearyl ammonium chloride for example, also alkyl trialkyl ammonium salts, for example cetyl trimethyl ammonium chloride or bromide, alkyl dimethyl hydroxyethyl ammonium chlorides or bromides, dialkyl dimethyl ammonium chlorides or bromides, alkyl amide ethyl trimethyl ammonium ether sulfates, alkyl pyridinium salts, for example lauryl or cetyl pyrimidinium chloride, imidazoline derivatives and compounds having a cationic character such as amine oxides, for example alkyl dimethyl amine oxides or alkyl aminoethyl dimethyl amine oxides. Cetyl trimethyl ammonium salts are particularly advantageously used.

Amphoteric surfactants which can advantageously be used are
  acyl/dialkyl ethylene diamine, for example sodium acyl amphoacetate, disodium acyl amphodipropionate, disodium alkyl amphodiacetate, sodium acyl amphohydroxypropyl sulfonate, disodium acyl amphodiacetate and sodium acyl amphopropionate,
  N-alkyl amino acids, for example aminopropyl alkyl glutamide, alkyl aminopropionic acid, sodium alkyl imidodipropionate and lauroamphocarboxyglycinate.

Non-ionic surfactants which can advantageously be used are
  alcohols,
  alkanolamides, such as cocamides MEA/DEA/MIPA,
  amine oxides, such as cocamidopropylamine oxide,
  esters produced by esterification of carboxylic acids with ethylene oxide, glycerol, sorbitan or other alcohols,
  ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides such as lauryl glucoside, decyl glycoside and cocoglycoside.
  sucrose esters, ethers
  polyglycerol esters, diglycerol esters, monoglycerol esters
  methyl glucose esters, esters of hydroxy acids The use of a combination of anionic and/or amphoteric surfactants with one or more non-ionic surfactants is also advantageous.

The surface-active substance can be present in the blackberry leaf extract-containing preparations according to the invention in a concentration of between 1 and 98 wt. %, relative to the total weight of the preparations.

Cosmetic or dermatological preparations containing the blackberry leaf extract according to the invention can also be in the form of emulsions.

The oil phase of cosmetic, dermatological and/or pharmaceutical preparations according to the invention can advantageously be chosen from the following group of substances:
  mineral oils, mineral waxes
  fatty oils, fats, waxes and other natural and synthetic fat bodies, preferably esters of fatty acids with low C-number alcohols, for example with isopropanol, propylene glycol or glycerol, or esters of fatty alcohols with low C-number alkanoic acids or with fatty acids;
  alkyl benzoates;
  silicone oils such as dimethyl polysiloxanes, diethyl polysiloxanes, diphenyl polysiloxanes and mixed forms thereof.

Substances which can advantageously be used are (a) esters of saturated and/or unsaturated branched and/or unbranched alkane carboxylic acids having a chain length of 3 to 30 C atoms and saturated and/or unsaturated, branched and/or unbranched alcohols having a chain length of 3 to 30 C atoms, (b) esters of aromatic carboxylic acids and saturated and/or unsaturated, branched and/or unbranched alcohols having a chain length of 3 to 30 C atoms. Preferred ester oils are isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyl decyl stearate, 2-octyl dodecyl palmitate, oleyl oleate, oleyl erucate, erucyl oleate, erucyl erucate and synthetic, semisynthetic and natural mixtures of such esters, e.g. jojoba oil.

The oil phase can also advantageously be chosen from the group consisting of branched and unbranched hydrocarbons and hydrocarbon waxes, silicone oils, dialkyl ethers, the group consisting of saturated or unsaturated, branched or unbranched alcohols, and of fatty acid triglycerides, in particular the triglycerol esters of saturated and/or unsaturated, branched and/or unbranched alkane carboxylic acids having a chain length of 8 to 24, in particular 12 to 18 C atoms. The fatty acid triglycerides can advantageously be chosen from the group comprising synthetic, semisynthetic and natural oils, e.g. olive oil, sunflower oil, soya bean oil, groundnut oil, rapeseed oil, almond oil, palm oil, coconut oil, palm kernel oil and the like. Any blends of such oil and wax components can also advantageously be used. In some cases it is also advantageous to use waxes, for example cetyl palmitate, as the sole lipid component of the oil phase, the oil phase advantageously being chosen from the group consisting of 2-ethylhexyl isostearate, octyl dodecanol, isotridecyl isononanoate, isoeicosane, 2-ethylhexyl cocoate, $C_{12-15}$-alkyl benzoate, caprylic-capric acid triglyceride and dicaprylyl ether. Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous. The hydrocarbons paraffin oil, squalane and squalene can also advantageously be used. The oil phase can advantageously also display a content of cyclic or linear silicone oils or consist entirely of such oils, it being preferable, however, to use an additional content of other oil phase components along with the silicone oil or silicone oils. Cyclomethicone (e.g. decamethyl cyclopentasiloxane) can advantageously be used as the silicone oil. Other silicone oils can also advantageously be used, however, for example undecamethyl cyclotrisiloxane, polydimethyl siloxane and poly(methylphenyl siloxane). Mixtures of cyclomethicone and isotridecyl isononanoate and of cyclomethicone and 2-ethylhexyl isostearate are also particularly advantageous.

The aqueous phase of blackberry leaf extract-containing preparations in the form of an emulsion can advantageously include: alcohols, diols or polyols having a low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, also alcohols having a low C number, e.g. ethanol, isopropanol, 1,2-propanediol, glycerol and in particular one or more thickeners, which can advantageously be chosen from the group comprising silicon dioxide, aluminium silicates, polysaccharides or derivatives thereof, e.g. hyaluronic acid, xanthan gum, hydroxypropyl methyl cellulose, particularly advantageously from the group of polyacrylates, preferably a polyacrylate from the group of so-called carbopols, for example type 980, 981, 1382, 2984, 5984 carbopols, either individually or in combination.

Preparations containing blackberry leaf extract according to the invention and in the form of an emulsion advantageously include one or more emulsifiers. O/W emulsifiers, for example, can advantageously be chosen from the group of polyethoxylated or polypropoxylated or polyethoxylated and polypropoxylated products, e.g.:

fatty alcohol ethoxylates
ethoxylated wool wax alcohols,
polyethylene glycol ethers having the general formula R—O—(—CH$_2$—CH$_2$—O—)$_n$—R',
fatty acid ethoxylates having the general formula R—COO—(—CH$_2$—CH$_2$—O—)$_n$—H,
etherified fatty acid ethoxylates having the general formula R—COO—(—CH$_2$—CH$_2$—O—)$_n$—R', esterified fatty acid ethoxylates having the general formula R—COO—(—CH$_2$—CH$_2$—O—)$_n$—C(O)—R', polyethylene glycol glycerol fatty acid esters
ethoxylated sorbitan esters
cholesterol ethoxylates
ethoxylated triglycerides
alkyl ether carboxylic acids having the general formula R—COO—(—CH$_2$—CH$_2$—O—)$_n$—OOH, where $n$ represents a number from 5 to 30, polyoxyethylene sorbitol fatty acid esters,
alkyl ether sulfates having the general formula R—O—(—CH$_2$—CH$_2$—O—)$_n$—SO$_3$—H
fatty alcohol propoxylates having the general formula R—O—(—CH$_2$—CH(CH$_3$)—O—)$_n$—H
polypropylene glycol ethers having the general formula R—O—(—CH$_2$—CH(CH$_3$)—O—)$_n$—R' propoxylated wool wax alcohols,
etherified fatty acid propoxylates R—COO—(—CH$_2$—CH(CH$_3$)—O—)$_n$—R'
esterified fatty acid propoxylates having the general formula R—COO—(—CH$_2$—CH(CH$_3$)—O—)$_n$—C(O)—R' fatty acid propoxylates having the general formula

R—COO—(—CH$_2$—CH(CH$_3$)—O—)$_n$—H, polypropylene glycol glycerol fatty acid esters
propoxylated sorbitan esters,
cholesterol propoxylates
propoxylated triglycerides
alkyl ether carboxylic acids having the general formula R—O—(—CH$_2$—CH(CH$_3$)—O—)$_n$—CH$_2$—COOH, alkyl ether sulfates or the acids underlying these sulfates having the general formula R—O—(—CH$_2$—CH(CH$_3$)—O—)$_n$—SO$_3$—H,
fatty alcohol ethoxylates/propoxylates having the general formula R—O—X$_n$—Y$_m$—H
polypropylene glycol ethers having the general formula R—O—X$_n$—Y$_m$—R'
etherified fatty acid propoxylates having the general formula R—COO—X$_n$—Y$_m$—R'
fatty acid ethoxylates/propoxylates having the general formula R—COO—X$_n$—Y$_m$—H.

Particularly advantageously according to the invention the polyethoxylated or polypropoxylated or polyethoxylated and polypropoxylated O/W emulsifiers are chosen from the group of substances having HLB values of 11 to 18, most particularly advantageously having HLB values of 14.5 to 15.5, if the O/W emulsifiers display saturated R and R' radicals. If the O/W emulsifiers display unsaturated R and/or R' radicals, or if isoalkyl derivatives are present, the preferred HLB value of such emulsifiers can also be lower or higher.

It is advantageous to choose the fatty alcohol ethoxylates from the group of ethoxylated stearyl alcohols, cetyl alcohols, cetyl stearyl alcohols (cetearyl alcohols). Particularly preferred are:

Polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is also advantageous to choose the fatty acid ethoxylates from the following group:

Polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14)

oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

Sodium laureth-11 carboxylate can advantageously be used as the ethoxylated alkyl ether carboxylic acid or its salt. Sodium laureth 1-4 sulfate can advantageously be used as the alkyl ether sulfate. Polyethylene glycol (30) cholesteryl ether can advantageously be used as the ethoxylated cholesterol derivative. Polyethylene glycol (25) soya sterol has also proved itself.

Polyethylene glycol (60) evening primrose glycerides can advantageously be used as the ethoxylated triglycerides.

It is also advantageous to choose the polyethylene glycol glycerol fatty acid esters from the group comprising polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise advantageous to choose the sorbitan esters from the group comprising polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be used as advantageous W/O emulsifiers: fatty alcohols having 8 to 30 carbon atoms, monoglycerol esters of saturated and/or unsaturated, branched and/or unbranched alkane carboxylic acids having a chain length of 8 to 24, in particular 12 to 18 C atoms, diglycerol esters of saturated and/or unsaturated, branched and/or unbranched alkane carboxylic acids having a chain length of 8 to 24, in particular 12 to 18 C atoms, monoglycerol ethers of saturated and/or unsaturated, branched and/or unbranched alcohols having a chain length of 8 to 24, in particular 12 to 18 C atoms, diglycerol ethers of saturated and/or unsaturated, branched and/or unbranched alcohols having a chain length of 8 to 24, in particular 12 to 18 C atoms, propylene glycol esters of saturated and/or unsaturated, branched and/or unbranched alkane carboxylic acids having a chain length of 8 to 24, in particular 12 to 18 C atoms and sorbitan esters of saturated and/or unsaturated, branched and/or unbranched alkane carboxylic acids having a chain length of 8 to 24, in particular 12 to 18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monostearate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

Preferred embodiments and other aspects of the present invention follow from the appended claims and the examples below together with the figures, wherein the drawings and examples are not intended to limit the invention:

Example 1: Preparation of Blackberry Leaves Ethanol/Water 3:7 Extract 700 g of an ethanol/water 3:7 (m/m) mixture are added to 44 g of dried chopped blackberry leaves and the mixture is stirred for two hours with reflux at a temperature of 80-100° C. After cooling the extraction mixture to room temperature it is filtered through a pleated filter and the clear filtrate is evaporated to dryness under vacuum in a rotary evaporator. 12 g (yield 27.3%) of blackberry leaf extract are obtained.

Characterisation by HPLC fingerprint analysis: Column: YMC ODS-AQ, 5 μm, 150×3 mm with precolumn, temperature: 40° C., flow rate: 0.6 ml/min, acetonitrile/water with 0.1% formic acid gradient, injection volume: 5 μl, detection wavelength: 254 nm. FIG. 1 shows the HPLC diagram obtained.

Example 2: Determination of the Total Polyphenol Content

The total polyphenol content is determined photometrically, the content being calculated as catechin equivalents using a catechin calibration curve.

To prepare the EDTA solution, 2.15 g of Titriplex III and 29.0 g of sodium hydroxide are dissolved with distilled water in a 1 l measuring flask. A 0.5-1% solution of the extract to be determined is prepared in distilled water. For the calibration curve catechin solutions of various concentrations in the range from 0.02 to 0.10 mg/ml are prepared in distilled water. 7.5 ml of distilled water, 1.5 ml of the EDTA solution, 1 ml of catechin solution or 1 ml of extract solution and 0.5 ml of Folin-Denis reagent are mixed together and left to stand for 30 minutes at room temperature. In parallel, 1 ml of distilled water is prepared in the same way as a blank control. The absorption of the catechin and extract samples at 760 nm is then measured against the blank control.

A calibration curve is produced from the catechin absorption measurement values. The total polyphenol content of the extract is calculated using the equation below:

$$\% \text{ Catechin equivalents} = \frac{\text{mg/ml catechin equivalents from the calibration curve}}{\text{mg/ml weighed portion of extract}} \times 100$$

Example 3: Anti-Mmp Assays

A 96-well microtitre plate (MMP Biotrak, Activity Assay System, Amersham Biosciences) coated with anti-MMP antibodies is incubated overnight (4° C.) with a pro-MMP solution standardised to 2 ng/ml (Amersham Biosciences). In parallel, a multistep pro-MMP standard series in the concentration range from 0.125 to 2 ng/ml is incubated to produce a regression line.

Removal of the solutions from the wells is followed by activation for 3 hours at 37° C. with p-aminophenyl mercuric acetate (APMA) [MMP-9: 1 mM; MMP-1: 0.025 mM]. Following removal of the APMA solution from the wells, incubation is performed with the extracts to be tested, prediluted in assay buffer, or with pure assay buffer as a control, at 37° C. for 15 minutes. After incubation and removal of the solutions from the wells, the enzyme/substrate solution provided in the assay kit is added in the final step and incubated for at least a further 4 hours at 37° C. The yellowish colour change of the reaction solutions accompanying the final incubation step is measured in the photometer at 405 nm.

Calculation of the Results:

All average absorption values are corrected by the average absorption value of the "0" standard (STDO: assay buffer) and divided by the square of the necessary incubation time.

$$\frac{\Delta Abs_{t_1}}{h^2} \cdot 1000 = \frac{Abs_{t_1}(x) - Abs_{t_1}(STD0)}{h^2} \cdot 1000$$

where $h$ = incubation time in $[h]$

The time-corrected absorption values are plotted against the MMP concentrations of the standard series used. The MMP concentration recovered per well is determined from the resulting regression lines.

The inhibition I is calculated from the ratio of recovered MMP concentration $c_r$ and the nominal concentration of the blank $c_{nom}$ (2 ng/ml):

$$I[\%] = \left(1 - \frac{c_r}{c_{nom}}\right) \cdot 100$$

The $EC_{50}$ is calculated for each extract from the MMP inhibition [%] in a series of dilutions of tested samples. This is the concentration of an extract at which MMP activity is inhibited by 50%.

Results

TABLE 1

MMP-9 inhibition by various *Rubus* extracts

| Extract | Inhibition in % at a concentration of | | | | $EC_{50}$ [%] |
|---|---|---|---|---|---|
| | 0.1% | 0.01% | 0.001% | 0.0001% | |
| Blackberry (*R. fruticosus*) leaves ethanol/water 1:1 extract | 70.52 ± 4.11 | 61.57 ± 4.52 | 58.65 ± 2.70 | −0.55 ± 12.25 | 0.0006 |
| Raspberry (*R. idaeus*) leaves ethanol/water 1:1 extract | 84.10 ± 14.17 | 40.53 ± 15.33 | 12.94 ± 32.86 | n.d. | 0.0165 |
| Blackberry (*R. fruticosus*) fruit juice concentrate (65 Brix) | 55.66 ± 12.73 | 18.72 ± 4.92 | 9.90 ± 0.48 | n.d. | 0.0703 | n.d. = not determined

TABLE 2

MMP-1 inhibition by various *Rubus* extracts

| Extract | Inhibition in % at a concentration of | | | | $EC_{50}$ [%] |
|---|---|---|---|---|---|
| | 0.1% | 0.01% | 0.001% | 0.0001% | |
| Blackberry (*R. fruticosus*) leaves ethanol/water 1:1 extract | 91.41 ± 2.67 | 61.75 ± 4.65 | 50.78 ± 8.93 | 21.73 ± 6.34 | 0.0009 |
| Raspberry (*R. idaeus*) leaves ethanol/water 1:1 extract | 88.73 ± 1.41 | 56.24 ± 3.43 | 34.13 ± 3.14 | n.d. | 0.0052 |
| Blackberry (*R. fruticosus*) fruit juice concentrate (65 Brix) | 54.56 ± 19.64 | 33.63 ± 10.07 | −1.98 ± 3.87 | n.d. | 0.0606 | n.d. = not determined

TABLE 3

MMP-9 inhibition by various blackberry leaf extracts

| Extractant | Inhibition in % at a concentration of | | | | $EC_{50}$ [%] |
|---|---|---|---|---|---|
| | 0.1% | 0.01% | 0.001% | 0.0001% | |
| Water | 55.79 ± 7.14 | 26.14 ± 7.51 | 35.47 ± 3.37 | 2.72 ± 3.86 | 0.0302 |
| Ethanol/water 3:7 | 71.08 ± 0.90 | 70.67 ± 4.54 | 59.27 ± 5.58 | 10.84 ± 17.17 | 0.0006 |
| Ethanol/water 1:1 | 70.52 ± 4.11 | 61.57 ± 4.52 | 58.65 ± 2.70 | −0.55 ± 12.25 | 0.0006 |
| Ethanol/water 7:3 | 77.44 ± 1.36 | 47.36 ± 4.53 | 51.00 ± 7.26 | 11.60 ± 14.17 | 0.0038 |
| Ethanol | 78.94 ± 0.29 | 63.31 ± 4.44 | 38.31 ± 8.49 | 18.61 ± 9.25 | 0.0029 |

TABLE 4

MMP-1 inhibition by various blackberry leaf extracts

| | Inhibition in % at a concentration of | | | | |
|---|---|---|---|---|---|
| Extractant | 0.1% | 0.01% | 0.001% | 0.0001% | $EC_{50}$ [%] |
| Water | 90.36 ± 4.66 | 53.87 ± 9.19 | 29.74 ± 4.32 | n.d. | 0.0069 |
| Ethanol/water 3:7 | 103.21 ± 1.14 | 74.60 ± 5.35 | 81.41 ± 1.53 | 22.74 ± 12.84 | 0.0007 |
| Ethanol/water 1:1 | 91.41 ± 2.67 | 61.75 ± 4.65 | 50.78 ± 8.93 | 21.73 ± 6.34 | 0.0009 |
| Ethanol/water 7:3 | 96.93 ± 7.28 | 83.37 ± 2.27 | 72.14 ± 0.78 | 10.86 ± 11.46 | 0.0004 |
| Ethanol | 102.97 ± 2.32 | 84.38 ± 1.59 | 49.38 ± 15.89 | 0.61 ± 9.27 | 0.0010 | n.d. = not determined

This data verifies that blackberry leaf extract displays an outstanding MMP-9 and MMP-1 inhibiting action.

TABLE 5

Comparison of tannin content (determined according to Folin-Denis, expressed in catechin equivalents) and anti-MMP activity of various blackberry leaf extracts

| Extractant | Tannin content [%] | MMP-9 inhibition $EC_{50}$ [%] | MMP-1 inhibition $EC_{50}$ [%] |
|---|---|---|---|
| Water | 20.2 | 0.0302 | 0.0069 |
| Ethanol/water 3:7 | 20.6 | 0.0006 | 0.0007 |
| Ethanol/water 1:1 | 20.2 | 0.0006 | 0.0009 |
| Ethanol/water 7:3 | 18.8 | 0.0038 | 0.0004 |
| Ethanol | 11.9 | 0.0029 | 0.0010 |

Example 4: Other Cosmetic/Dermatological Application Examples

For use, the blackberry leaf extract-containing dermatological and cosmetic preparations in combination with other cosmetic active ingredients and additives are applied to the skin and/or the hair in an adequate amount in the conventional way for cosmetics. Advantageous preparations for a number of applications are cited below by way of example:

4.1 Antiwrinkle W/O Cream

| Part | Raw material name (manufacturer) | INCI name | Content in wt. % |
|---|---|---|---|
| A | Dragosan W/O P (Symrise) | Sorbitan Isostearate, Hydrogenated Castor Oil, Ceresin, Beeswax (Cera Alba) | 8.00 |
| | Dragoxat EH (Symrise) | Ethylhexyl Ethylhexanoate | 8.00 |
| | Isodragol (Symrise) | Triisononanoin | 8.00 |
| | Dow Corning 200 Fluid (300 cs) (Dow Corning) | Dimethicone | 2.00 |
| | Betone Gel Mio (Elementis) | Mineral Oil, Quaternium-18 Hectorite, Propylene Carbonate | 3.00 |
| B | Demineralised water | Water (Aqua) | 59.90 |
| | Magnesium sulfate hepta hydrate (Merck) | Magnesium Sulfate | 1.00 |
| | Glycerin, 99.5% | Glycerin | 3.00 |
| | Drago-Beta-Glucan (Symrise) | Water (Aqua), Butylene Glycol, Glycerin, Avena Sativa (Oat) Kernel Extract | 5.00 |
| | Blackberry leaf extract | | 1.00 |
| | Dragocid Liquid (Symrise) | Phenoxyethanol, Methylparaben, Ethylparaben, Butylparaben, Propylparaben, Isobutylparaben | 0.80 |
| C | Symrise perfume oil | Fragrance | 0.30 |

Heat part A and B without Drago-Beta-Glucan to 75° C. Add Drago-Beta-Glucan to part B. Add part B to part A and emulsify. Cold-stir the emulsion, homogenise again at approx. 50° C. and add the perfume oil at approx. 35° C.

4.2 Anti-Skin-Ageing Night Cream

| Part | Raw material name (manufacturer) | INCI name | Content in wt. % |
|---|---|---|---|
| A | Dragosan W/O P (Symrise) | Sorbitan Isostearate, Hydrogenated Castor Oil, Ceresin, Beeswax (Cera Alba) | 6.00 |
| | PCL-Liquid (Symrise) | Cetearyl Ethylhexanoate, Isopropyl Myristate | 12.00 |
| | Sunflower oil (H. Erhard Wagner) | *Helianthus Annuus* (Sunflower) Seed Oil | 5.00 |
| | Sweet almond oil (H. Er hard Wagner) | *Prunus dulcis* | 5.00 |
| | Dragosan W/O Liquid (Symrise) | Polyglyceryl-3-Polyricinoleate, Sorbitan Isostearate | 1.00 |
| | Alugel 34 TH (Baerlocher) | Aluminium Stearate | 1.00 |
| | Oxynex 2004 (Merck) | Bht | 0.10 |
| B | Demineralised water | Water (Aqua) | 56.20 |
| | Glycerin, 99.5% | Glycerin | 2.00 |
| | Karion F (Merck) | Sorbitol | 2.00 |
| | *Aloe Vera* Gel Concentrate (Symrise) | Water (Aqua), *Aloe Barbadensis* Leaf Juice | 3.00 |
| | Extrapon *Hamamelis* distillate colourless (Symrise) | Propylene Glycol, *Hamamelis Virginiana* (Witch Hazel) Water, Water (Aqua), *Hamamelis Virginiana* (Witch Hazel) Extract | 1.00 |
| | Blackberry leaf extract | | 0.50 |
| | Magnesium sulfate hepta hydrate (Merck) | Magnesium Sulfate | 0.70 |
| | Dragocid Liquid (Symrise) | Phenoxyethanol, Methylparaben, Ethylparaben, Butylparaben, Propylparaben, Isobutylparaben | 0.80 |
| C | Vitamin E acetate (DSM Nutritional Products) | Tocopheryl Acetate | 3.00 |
| | Vitamin A palmitate in oil (1 mill. Ie/g) (DSM Nutrional Products) | Retinyl Palmitate | 0.20 |
| | -(-Alpha-)-Bisabolol, natural (Symrise) | Bisabolol | 0.10 |
| | Symrise perfume oil | Fragrance | 0.40 |

Heat part A and B separately to approx. 80° C. Add part B to part A, emulsify and cold-stir. Homogenise again at approx. 60° C. and add part C at approx. 35° C.

4.3 O/W Anti-Skin-Ageing Lotion with UVA/B Broadband Protection

| Part | Raw material name (manufacturer) | INCI name | Content in wt. % |
|---|---|---|---|
| A | Emulsiphos (Symrise) | Potassium Cetyl Phosphate, Hydrogenated Palm Glycerides | 1.50 |
| | Tegosoft TN (Degussa) | C12-15 Alkyl Benzoate | 5.00 |
| | Copherol 1250 (Cognis) | Tocopheryl Acetate | 0.50 |
| | Lanette O (Cognis) | Cetearyl Alcohol | 1.00 |
| | Neutral oil (Symrise) | Caprylic/Capric Triglyceride | 2.00 |
| | Dow Corning 246 Fluid (Dow Corning) | Cyclohexasiloxane (and) Cyclopentasiloxane | 2.00 |
| | Neo Heliopan AV (Symrise) | Ethylhexyl Methoxycinnamate | 3.00 |
| | Neo Heliopan OS (Symrise) | Ethylhexyl Salicylate | 5.00 |
| | Neo Heliopan MBC (Symrise) | 4-Methylbenzylidene Camphor | 1.50 |
| | Neo Heliopan 357 (Symrise) | Butyl Methoxydibenzoylmethane | 1.00 |
| | EDETA DB (BASF) | Disodium EDTA | 0.10 |
| | Keltrol T (Danby-Chemie) | Xanthan Gum | 0.20 |
| | Carbopol ETD 2050 (Noveon) | Carbomer | 0.20 |

| Part | Raw material name (manufacturer) | INCI name | Content in wt. % |
|---|---|---|---|
| B | Demineralised water | Water (Aqua) | 59.08 |
| | Glycerin, 99.5% | Glycerin | 4.70 |
| | Dragocid Liquid (Symrise) | Phenoxyethanol, Methylparaben, Ethylparaben, Butylparaben, Propylparaben, Isobutylparaben | 0.70 |
| | Neo Heliopan AP (22% aq. solution neutralised with triethanolamine) (Symrise) | Disodium Phenyl Dibenzimidazole Tetrasulfonate | 4.55 |
| | Neo Heliopan Hydro (30% aq. solution neutralised with triethanolamine) (Symrise) | Phenylbenzimidazole Sulfonic Acid | 6.67 |
| | Blackberry leaf extract | | 0.30 |
| C | Triethanolamine, 99% | Triethanolamine | 0.50 |
| D | Symrise perfume oil | Fragrance | 0.40 |
| | Dragosantol (Symrise) | Bisabolol | 0.10 |

Heat part A (up to Keltrol and Carbopol) to 85° C. Add Keltrol and Carbopol and homogenise. Heat part B to 85° C. and add part B to part A. Add part C directly to part NB, homogenise and leave to cool. Add part D to part A/B/C and homogenise. The pH of the end product should be around 7.2 to 7.5.

4.4 Anti-Skin-Ageing after-Sun Lotion (O/W)

| Part | Raw material name (manufacturer) | INCI name | Content in wt. % |
|---|---|---|---|
| A | Demineralised water | Water (Aqua) | 71.40 |
| | Glycerin, 99.5% | Glycerin | 4.00 |
| | D-Panthenol (BASF) | Panthenol | 1.00 |
| | Butylene glycol | Butylene Glycol | 5.00 |
| | Allantoin (Merck) | Allantoin | 0.10 |
| | Aloe Vera Gel Concentrate 10/1 (Symrise) | Water (Aqua), *Aloe Barbadensis* Leaf Juice | 3.0 |
| | Blackberry leaf extract | | 1.00 |
| | Lara Care A-200 (Rahn) | Galactoarabinan | 0.25 |
| B | Baysilone Oil M 350 (GE Bayer Silicones) | Dimethicone | 1.00 |
| | Copherol 1250 (Cognis) | Tocopheryl Acetate | 0.50 |
| | Tegosoft TN (Degussa) | C12-15 Alkyl Benzoate | 5.00 |
| | Cetiol SB 45 (Cognis) | *Butyrospermum Parkii* (Shea Butter) | 1.00 |
| | Cetiol OE (Cognis) | Dicaprylyl Ether | 4.00 |
| | -(-Alpha-)-Bisabolol, natural (Symrise) | Bisabolol | 0.10 |
| | Dragocid Liquid (Symrise) | Phenoxyethanol, Methylparaben, Ethylparaben, Butylparaben, Propylparaben, Isobutylparaben | 0.70 |
| | Pemulen TR-2 (Noveon) | Acrylates/C10-30 Alkyl Acrylate Crosspolymer | 0.25 |
| | Frescolat ML cryst. (Symrise) | Menthyl Lactate | 0.80 |
| | Symrise perfume oil | Fragrance | 0.30 |
| C | Sodium hydroxide (10% aq. solution) | Sodium Hydroxide | 0.60 |

Dissolve part A in water. Dissolve Frescolat ML cryst. and Cetiol SB 45 from part B in Tegosoft TN whilst heating to a maximum of 35° C., allow to cool and add the remaining constituents from part B. Add part B to part A whilst stirring and homogenise. The pH of the end product should be around 6.0.

| Part | Raw material name (manufacturer) | INCI name | Content in wt. % |
|---|---|---|---|
| A | Dracorin GOC (Symrise) | Glyceryl Oleate Citrate, Caprylic/Capric Triglyceride | 2.00 |
| | Neutral oil | Caprylic/Capric Triglyceride | 4.00 |
| | Paraffin oil 5 grade E (Parafluid) | Paraffinum Liquidum | 4.00 |
| | PCL Liquid 100 (Symrise) | Cetearyl Ethylhexanoate | 7.00 |
| | Dragoxat EH (Symrise) | Ethylhexyl Ethylhexanoate | 4.00 |

| Part | Raw material name (manufacturer) | INCI name | Content in wt. % |
|---|---|---|---|
| | Dow Corning 345 Fluid (Dow Corning) | Cyclomethicone | 0.50 |
| | Dragosantol (Symrise) | Bisabolol | 0.10 |
| | Symrise perfume oil | Fragrance | 0.20 |
| B | Demineralised water | Water (Aqua) | 71.50 |
| | Pemulen TR-2 (Noveon) | Acrylates/C10-30 Alkyl Acrylate Crosspolymer | 0.20 |
| | Hydrolite-5 (Symrise) | Pentylene Glycol | 5.00 |
| | Drago-Oat-Active (Symrise) | Water (Aqua), Butylene Glycol, *Avena Sativa* (Oat) Kernel Extract | 1.00 |
| | Blackberry leaf extract | | 0.10 |
| C | Sodium hydroxide (10% aq. solution) | Sodium Hydroxide | 0.40 |

4.5 Anti-Skin-Ageing O/W Body Spray

Swell Pemulen in water, then add the remaining raw materials from part B. Mix part A. Add part B without stirring to part A, and only then emulsify. Add part C during emulsification. The pH of the end product should be around 6.3.

4.6 Anti-Skin-Ageing O/W Cream

| Part | Raw material name (manufacturer) | INCI name | Content in wt. % |
|---|---|---|---|
| A | Dracorin GMS (Symrise) | Glyceryl Stearate | 2.00 |
| | PCL-Solid (Symrise) | Stearyl Heptanoate, Stearyl Caprylate | 2.00 |
| | Lanette O (Cognis) | Cetearyl Alcohol | 3.00 |
| | PCL Liquid 100 (Symrise) | Cetearyl Ethylhexanoate | 5.00 |
| | Isodragol (Symrise) | Triisononanoin | 2.00 |
| | Abil 350 (Degussa-Goldschmidt) | Dimethicone | 2.00 |
| | Dragoxat EH (Symrise) | Ethylhexyl Ethylhexanoate | 3.00 |
| B | Demineralised water | Water (Aqua) | 69.35 |
| | Carbopol Ultrez-10 (Noveon) | Carbomer | 0.10 |
| | Keltrol RD (CP-Kelco) | Xanthan Gum | 0.10 |
| | Emulsiphos (Symrise) | Potassium Cetyl Phosphate, Hydrogenated Palm Glycerides | 2.00 |
| | Dragocid Liquid (Symrise) | Phenoxyethanol, Methylparaben, Ethylparaben, Butylparaben, Propylparaben, Isobutylparaben | 0.80 |
| | Extrapon Camomile GW (Symrise) | Glycerin, Water (Aqua), *Chamomilla Recutita* (Matricaria) Flower Extract | 0.50 |
| | Extrapon Rosemary GW (Symrise) | Glycerin, Water (Aqua), *Rosmarinus officinalis* (Rosemary) Leaf Extract | 0.30 |
| | Extrapon Green Tea GW (Symrise) | Glycerin, Water (Aqua), *Camellia Sinensis* Leaf Extract | 0.20 |
| | Blackberry leaf extract | | 0.10 |
| | Propylene glycol-1,2 99P GC | Propylene Glycol | 5.00 |
| | Glycerin 85 P. | Glycerin | 2.00 |
| C | Sodium hydroxide (10% aq. solution) | Sodium Hydroxide | 0.25 |
| D | Symrise perfume oil | Fragrance | 0.30 |

Pre-swell Carbopol Ultrez-10 and Keltrol RD in water and add the remaining raw materials from part B. Heat part A and B separately to approx. 80° C. Add part A to part B and emulsify whilst adding part C. Cold-stir and add part D at around 35° C. The pH of the end product should be around 5.5.

4.7 Anti-Skin-Ageing Shampoo

| Part | Raw material name (manufacturer) | INCI name | Content in wt. % |
|---|---|---|---|
| A | Genapol LRO Liquid (Cognis) | Sodium Laureth Sulfate | 37.00 |
|  | Dragoderm (Symrise) | Glycerin, *Triticum Vulgare* (Wheat) Gluten, Water (Aqua) | 2.00 |
|  | Blackberry leaf extract |  | 0.50 |
| B | Demineralised water | Water (Aqua) | 31.10 |
|  | Merquat 550 (Ondeo Nalco) | Polyquaternium-7 | 0.50 |
| C | Demineralised water | Water (Aqua) | 20.00 |
|  | Comperlan 100 (Cognis) | Cocamide MEA | 0.50 |
| D | Tego Betain L7 unconc. (Degussa-Goldschmidt) | Cocamidopropyl Betain | 6.00 |
|  | Citric acid 10% | Citric Acid | 0.30 |
|  | EDETA B Powder (BASF) | Tetrasodium EDTA | 0.10 |
|  | Sodium benzoate | Sodium Benzoate | 0.50 |
|  | Sodium chloride | Sodium Chloride | 1.00 |
|  | Symrise perfume oil | Fragrance | 0.50 |

Dissolve Dragoderm and blackberry leaf extract in Genapol LRO. Predissolve Merquat 550 in water and add. Dissolve part C whilst stirring and heating and allow to cool. Dissolve part C in part NB. Add the raw materials from part D one at a time and stir. The pH of the end product should be around 5.0.

4.8 Anti-Skin-Ageing O/W Cream

| Part | Raw material name (manufacturer) | INCI name | Content in wt. % |
|---|---|---|---|
| A | Dracorin CE (Symrise) | Glyceryl Stearate Citrate | 5.00 |
|  | Neutral oil (Symrise) | Caprylic/Capric Triglyceride | 6.00 |
|  | Isopropyl palmitate (Symrise) | Isopropyl Palmitate | 4.00 |
|  | Lanette 16 (Cognis) | Cetyl Alcohol | 1.00 |
|  | PCL Liquid 100 (Symrise) | Cetearyl Ethylhexanoate | 3.00 |
|  | Dragoxat EH (Symrise) | Ethylhexyl Ethylhexanoate | 3.00 |
|  | Abil 350 (Degussa-Goldschmidt) | Dimethicone | 0.50 |
| B | Demineralised water | Water (Aqua) | 72.90 |
|  | Keltrol RD (Rahn) | Xanthan Gum | 0.20 |
|  | Symdiol 68 (Symrise) | 1,2 Hexanediol, Caprylylglycol | 0.50 |
|  | Drago-Beta-Glucan (Symrise) | Water (Aqua), Butylene Glycol, Glycerin, *Avena Sativa* (Oat) Kernel Extract | 0.30 |
|  | Blackberry leaf extract |  | 0.30 |
|  | Glycerin 85 P. | Glycerin | 3.00 |
| C | Symrise perfume oil | Fragrance | 0.30 |

Swell Keltrol in water and add the remaining raw materials from part B up to Drago-Beta-Glucan. Heat part A and B separately to approx. 80° C. Add Drago-Beta-Glucan to part B. Add part B to part A, and only then emulsify. Cold-stir and add part C at around 35° C. The pH of the end product should be around 5.5.

Example 5: Other Application Examples in the Area of Oral Hygiene

For use, the blackberry leaf extract-containing oral hygiene products according to the invention in combination with other active ingredients and additives are introduced into the oral cavity in an adequate amount in the conventional way. Advantageous preparations for a number of applications are cited below by way of example. Unless otherwise specified, all figures stated relate to the weight.

5.1. Gel Toothpaste with Activity Against Bad Breath

|  | I (%) | II (%) | III (%) |
|---|---|---|---|
| Na carboxymethyl cellulose | 0.40 | 0.40 | 0.40 |
| Sorbitol 70%, in water | 72.00 | 72.00 | 72.00 |
| Polyethylene glycol (PEG) 1500 | 3.00 | 3.00 | 3.00 |
| Na saccharinate | 0.07 | 0.07 | 0.07 |
| Na fluoride | 0.24 | 0.24 | 0.24 |
| p-Hydroxybenzoic acid (PHB) ethyl ester | 0.15 | 0.15 | 0.15 |
| Aroma A (see below) | 0.10 | 0.80 | 0.75 |
| Blackberry leaf extract | 0.01 | 0.40 | 1.00 |
| Abrasive silica | 11.00 | 11.00 | 11.00 |
| Thickening silica | 6.00 | 6.00 | 6.00 |
| Sodium dodecyl sulfate (SDS) | 1.40 | 1.40 | 1.40 |
| Water dist. | To make 100.00 | To make 100.00 | To make 100.00 |

Aroma A had the following composition:

30 wt. % l-menthol, 30 wt. % peppermint oil *Mentha piperita,* 21.5 wt. % peppermint oil *Mentha arvensis,* 9 wt. % anethol, 0.5 wt. % anisaldehyde, 2 wt. % eucalyptol, 1 wt. % *Eucalyptus globulus* oil, 3 wt. % menthone, 1 wt. % spearmint oil, 1 wt. % basil oil, 0.5 wt. % menthyl acetate, 0.05 wt. % menthyl lactate, 0.1 wt. % menthyl-3-carboxylic acid-N-ethylamide (WS-3), 0.05 wt. % 2-hydroxyethyl menthyl carbonate (Frescolat MGC, Symrise), 0.05 wt. % 2-hydroxypropyl menthyl carbonate (Frescolat MPC, Symrise), 0.1 wt. % pinene, 0.1 wt. % propylene glycol, 0.05 wt. % limonene.

5.2. Toothpaste with Activity Against Plaque

| | I (%) | II (%) | III (%) |
|---|---|---|---|
| Na carboxymethyl cellulose | 1.00 | 1.00 | 1.00 |
| Glycerin | 12.50 | 12.50 | 12.50 |
| Sorbitol 70%, in water | 29.00 | 29.00 | 29.00 |
| Na saccharinate | 0.20 | 0.20 | 0.20 |
| Na fluoride | 0.22 | 0.22 | 0.22 |
| Azacycloheptane-2,2-diphosphoric acid, disodium salt | 1.00 | 1.00 | 1.00 |
| Bromochlorophene | 0.10 | 0.10 | 0.10 |
| Peppermint aroma | 0.05 | 1.10 | 0.35 |
| Blackberry leaf extract on silica (support mass: 1 g) | 1.05 | 1.30 | 1.70 |
| *Camomile* extract (Cremogen Forte *Camomile,* Symrise) | 0.20 | 0.50 | 0.10 |
| Sage extract (Extrapon Sage GW, Symrise) | 0.20 | 0.10 | 0.30 |
| Abrasive silica | 14.00 | 14.00 | 14.00 |
| Thickening silica | 5.00 | 5.00 | 5.00 |
| Sodium dodecyl sulfate (SDS) | 1.50 | 1.50 | 1.50 |
| Water dist. | To make 100.00 | To make 100.00 | To make 100.00 |

5.3. Toothpaste with Activity Against Plaque
Basis: silica, alkali diphosphate

| | I (%) | II (%) | III (%) |
|---|---|---|---|
| Carrageenan | 0.90 | 0.90 | 0.90 |
| Glycerin | 15.00 | 15.00 | 15.00 |
| Sorbitol 70%, in water | 25.00 | 25.00 | 25.00 |
| PEG 1000 | 3.00 | 3.00 | 3.00 |
| Na fluoride | 0.24 | 0.24 | 0.24 |
| Tetrapotassium diphosphate | 4.50 | 4.50 | 4.50 |
| Tetrasodium diphosphate | 1.50 | 1.50 | 1.50 |
| Na saccharinate | 0.40 | 0.40 | 0.40 |
| Precipitated silica | 20.00 | 20.00 | 20.00 |
| Titanium dioxide | 1.00 | 1.00 | 1.00 |
| PHB methyl ester | 0.10 | 0.10 | 0.10 |
| Menthol eucalyptol aroma | 1.10 | 0.80 | 0.20 |
| Blackberry leaf extract | 0.10 | 0.40 | 1.00 |
| *Aloe* extract (*Aloe vera* gel concentrate 10/1, Symrise) | 0.05 | 0.50 | 0.25 |
| Sodium dodecyl sulfate | 1.30 | 1.30 | 1.30 |
| Water dist. | To make 100.00 | To make 100.00 | To make 100.00 |

5.4. Toothpaste for Sensitive Teeth

| | I (%) | II (%) | III (%) |
|---|---|---|---|
| Na carboxymethyl cellulose | 0.70 | 0.70 | 0.70 |
| Xanthan gum | 0.50 | 0.50 | 0.50 |
| Glycerin | 15.00 | 15.00 | 15.00 |
| Sorbitol 70%, in water | 12.00 | 12.00 | 12.00 |
| K nitrate | 5.00 | 5.00 | 5.00 |
| Na monofluorophosphate | 0.80 | 0.80 | 0.80 |
| PHB methyl ester | 0.15 | 0.15 | 0.15 |
| PHB propyl ester | 0.05 | 0.05 | 0.05 |
| Na saccharinate | 0.20 | 0.20 | 0.20 |
| Menthol anethol aroma | 0.25 | 0.75 | 0.25 |
| Blackberry leaf extract | 0.02 | 1.00 | 1.50 |
| Rosemary extract (Extrapon Rosemary, Symrise) | 0.20 | 0.01 | 0.10 |
| Ca carbonate | 35.00 | 35.00 | 35.00 |
| Silicon dioxide | 1.00 | 1.00 | 1.00 |
| Sodium dodecyl sulfate (SDS) | 1.50 | 1.50 | 1.50 |
| Water dist. | To make 100.00 | To make 100.00 | To make 100.00 |

5.5. Toothpaste for Sensitive Teeth

| | I (%) | II (%) | III (%) |
|---|---|---|---|
| Hydroxyethyl cellulose | 1.40 | 1.40 | 1.40 |
| Guar gum | 0.60 | 0.60 | 0.60 |
| Glycerin | 18.00 | 18.00 | 18.00 |
| Sorbitol 70%, in water | 12.00 | 12.00 | 12.00 |
| Na saccharinate | 0.35 | 0.35 | 0.35 |
| Dye | 0.01 | 0.01 | 0.01 |
| PHB methyl ester | 0.15 | 0.15 | 0.15 |
| PHB propyl ester | 0.04 | 0.04 | 0.04 |
| Sr chloride | 10.50 | 10.50 | 10.50 |
| Peppermint aniseed aroma | 0.35 | 1.20 | 0.60 |
| Blackberry leaf extract | 0.05 | 0.50 | 0.90 |
| Green tea extract (Extrapon Green Tea GW, Symrise) | 0.25 | 0.10 | 0.05 |
| Precipitated silica | 15.00 | 15.00 | 15.00 |
| Silicon dioxide | 1.60 | 1.60 | 1.60 |
| Sodium dodecyl sulfate | 1.30 | 1.30 | 1.30 |
| Water dist. | To make 100.00 | To make 100.00 | To make 100.00 |

5.6. Ready-to-Use Mouthwash with Fluoride

| | I (%) | II (%) | III (%) |
|---|---|---|---|
| Ethanol | 7.00 | 7.00 | 7.00 |
| Glycerin | 12.00 | 12.00 | 12.00 |
| Na fluoride | 0.05 | 0.05 | 0.05 |
| Pluronic F-127 ® (BASF, surface-active substance) | 1.40 | 1.40 | 1.40 |
| Na phosphate buffer pH 7.0 | 1.10 | 1.10 | 1.10 |
| Sorbic acid | 0.20 | 0.20 | 0.20 |
| Na saccharinate | 0.10 | 0.10 | 0.10 |
| Menthol peppermint aroma | 0.08 | 0.20 | 0.15 |
| Blackberry leaf extract | 0.02 | 0.70 | 0.10 |
| Bisabolol | 0.01 | 0.05 | 0.20 |
| *Melissa* extract (Extrapon *Melissa,* Symrise) | 0.30 | 0.50 | 0.05 |
| Sage extract (Extrapon Sage, Symrise) | 0.30 | 0.10 | 0.05 |
| Dye | 0.01 | 0.01 | 0.01 |
| Water dist. | To make 100.00 | To make 100.00 | To make 100.00 |

5.7. Mouthwash Concentrate

| | I (%) | II (%) | III (%) |
|---|---|---|---|
| Ethanol, 95% | 80.00 | 80.00 | 80.00 |
| Na cyclamate | 0.15 | 0.15 | 0.15 |
| Menthol aniseed eucalyptol aroma | 1.50 | 2.00 | 2.00 |

-continued

|  | I (%) | II (%) | III (%) |
|---|---|---|---|
| Dye | 0.01 | 0.01 | 0.01 |
| Blackberry leaf extract | 1.50 | 2.50 | 5.00 |
| Green tea extract (Extrapon Green Tea GW, Symrise) | 0.20 | 1.00 | 0.50 |
| Bisabolol | 0.50 | 0.20 | 1.00 |
| Water dist. | To make 100.00 | To make 100.00 | To make 100.00 |

5.8. Chewing Gum

|  | I (%) | II (%) | III (%) |
|---|---|---|---|
| Chewing gum base | 21.00 | 21.00 | 21.00 |
| Glucose syrup | 16.50 | 16.50 | 16.50 |
| Glycerin | 0.50 | 0.50 | 0.50 |
| Icing sugar | 60.30 | 60.00 | 59.80 |
| Menthol spearmint aroma | 1.20 | 1.00 | 0.70 |
| Blackberry leaf extract | 0.50 | 1.00 | 1.50 |

5.9. Sugar-Free Chewing Gum

|  | I (%) | II (%) | III (%) |
|---|---|---|---|
| Chewing gum base | 30.00 | 30.00 | 30.00 |
| Sorbitol, powdered | 38.45 | 38.40 | 38.30 |
| Palatinite | 9.50 | 9.50 | 9.50 |
| Xylitol | 2.00 | 2.00 | 2.00 |
| Mannitol | 3.00 | 3.00 | 3.00 |
| Aspartame | 0.10 | 0.10 | 0.10 |
| Acesulfame K | 0.10 | 0.10 | 0.10 |
| Emulgum/emulsifier | 0.30 | 0.30 | 0.30 |
| Sorbitol 70%, in water | 14.00 | 14.00 | 14.00 |
| Glycerin | 1.00 | 1.00 | 1.00 |
| Menthol aniseed cinnamon aroma | 1.20 | 0.80 | 0.60 |
| Blackberry leaf extract | 0.35 | 0.80 | 1.10 |

5.10. Gelatine Capsule for Direct Consumption

|  | I (%) | II (%) | III (%) |
|---|---|---|---|
| Gelatine shell: |  |  |  |
| Glycerin | 2.014 | 2.014 | 2.014 |
| Gelatine 240 Bloom | 7.91 | 7.91 | 7.91 |
| Sucralose | 0.065 | 0.065 | 0.065 |
| Allura Red | 0.006 | 0.006 | 0.006 |
| Brilliant Blue | 0.005 | 0.005 | 0.005 |
| Core composition: |  |  |  |
| Plant oil triglyceride (coconut oil fraction) | 80.0 | 75.0 | 77.5 |
| Aroma B | 9.95 | 12.0 | 12.0 |
| Blackberry leaf extract | 0.05 | 3.0 | 0.5 |

Aroma B had the following composition (figures in wt. %):

0.1% neotame powder, 0.05% aspartame, 29.3% peppermint oil arvensis, 29.3% peppermint piperita oil Willamette, 2.97% sucralose, 2.28% triacetin, 5.4% diethyl tartrate, 12.1% peppermint oil yakima, 0.7% ethanol, 3.36% 2-hydroxyethyl menthyl carbonate, 3.0% 2-hydroxypropyl menthyl carbonate, 0.27% vanillin, 5.5% D-limonene, 5.67% L-menthyl acetate.

The gelatine capsule suitable for direct consumption (produced in an analogous way to WO 2004/050069) had a diameter of 5 mm and the weight ratio of core material to shell material was 90:10. The capsule opened in the mouth in less than 10 seconds and dissolved completely in less than 50 seconds.

The invention claimed is:

1. A product selected from the group consisting of a gel, oil-in-water emulsion, water-in-oil emulsion, a multiple emulsion, capsule, tablet, lotion, hypodispersion gel, chewing gum, tooth gel, and dental care chewing gum, wherein the product comprises a preparation for inhibiting metalloproteinase(s) MMP-1 and/or MMP-9 consisting essentially of an effective amount of a *Rubus fruticosus* leaf extract, wherein the *Rubus fruticosus* leaf extract is in solid form and is obtained by:
   a) adding an aqueous extractant containing water and an alcohol selected from the group consisting of methanol, ethanol, n-propanol, iso-propanol, where the ratio of alcohol to water is 2:8 to 8:2 to dried *Rubus fructicosus* leaves;
   b) extracting the dried *Rubus fruticosus* leaves with the extractant at a temperature of from 60° C. to 100° C. for a period of from 1 to 6 hours to obtain an extract;
   c) adding a pharmaceutically acceptable solid support, or a cosmetically acceptable solid support selected from the group consisting of (i) powdered maltrodextrin, lactose, silicon dioxide, glucose and a combination thereof, or (ii) starches, degraded starches, chemically or physically modified starches, modified celluloses, gum arabic, gum ghatti, tragacanth gum, karaya, carrageenan, pullulan, curdlan, xanthan gum, gellan gum, guar gum, locust bean gum, alginates, agar, pectin, inulin and a combination thereof to said extract to obtain a mixture; and,
   d) drying the mixture to provide a residual content of extractant of at most 5 wt. %, relative to the total weight of the extract obtained in step b) to obtain the solid *Rubus fruticosus* leaf extract.

2. The product of claim 1 wherein the alcohol is ethanol.

3. The product of claim 1 wherein the extractant contains a proportion of at least 20 wt. % of the alcohol.

4. The product of claim 1, wherein the extractant and water are present in a ratio of from 3:7 to 7:3.

5. The product of claim 1, wherein the drying step d) is spray-drying the extract of step (b) with the solid support of step (d) to form a powder.

6. A method of treating or reducing periodontitis or dental caries in a patient in need thereof consisting of orally administering to said patient an effective amount of an oral hygiene preparation selected from the group consisting of a tooth gel, chewing gum, or dental care chewing gum comprising 0.00001 wt. % to 20 wt. % of a *Rubus fruticosus* leaf extract in solid form by contacting the oral mucosa and teeth of the patient with the tooth gel, chewing gum, or dental care chewing gum in an amount effective to inhibit MMP-1 and MMP-9 activity in the oral mucosa and on the surface of the teeth, wherein the *Rubus fruticosus* leaf extract is obtained by:
   a) adding an aqueous extractant containing water and an alcohol: selected from the group consisting of methanol, ethanol, n-propanol, iso-propanol, where the ratio of alcohol to water is 2:8 to 8:2 to dried *Rubus fruticosus* leaves;
   b) extracting the dried *Rubus fruticosus* leaves with the extractant at a temperature of from 60° C. to 100° C. for a period of from 1 to 6 hours to obtain an extract;
   c) adding a pharmaceutically acceptable solid support, or a cosmetically acceptable solid support selected from the group consisting of (i) powdered maltrodextrin, lactose, silicon dioxide; glucose and mixtures thereof or (ii) starches, degraded starches, chemically or physically modified starches, modified celluloses, gum arabic, gum ghatti, tragacanth gum, karaya, carrageenan, pullulan, curdlan, xanthan gum, gellan gum, guar gum, locust bean gum, alginates, agar, pectin, inulin and a combination thereof to said extract to obtain a mixture; and, d) drying the mixture, to provide a residual content of extractant of at most 5 wt. %, relative to the total weight of the extract obtained in step b) to obtain the solid *Rubus fruticosus* leaf extract.

7. The method of claim 6, wherein the preparation is selected from the group consisting of a toothgel, a chewing gum and a dental care chewing gum and said method comprising contacting oral mucosa and teeth with the toothgel, chewing gum or dental care chewing gum to inhibit periodontitis and damage to teeth.

\* \* \* \* \*